United States Patent
Zhang et al.

(10) Patent No.: US 8,320,523 B2
(45) Date of Patent: *Nov. 27, 2012

(54) METHOD AND DEVICE FOR INSPECTION OF LIQUID ARTICLES

(75) Inventors: Li Zhang, Beijing (CN); Zhiqiang Chen, Beijing (CN); Xuewu Wang, Beijing (CN); Haifeng Hu, Beijing (CN); Hongxin Wu, Beijing (CN); Yuanjing Li, Beijing (CN); Yinong Liu, Beijing (CN); Ziran Zhao, Beijing (CN); Yuxiang Xing, Beijing (CN); Hu Tang, Beijing (CN); Yumin Yi, Beijing (CN); Jinyu Zhang, Beijing (CN)

(73) Assignees: Tshinghua University, Beijing (CN); Nuctech Company Limited, Beijing (CN)

( * ) Notice: Subject to any disclaimer, the term of this patent is extended or adjusted under 35 U.S.C. 154(b) by 0 days.

This patent is subject to a terminal disclaimer.

(21) Appl. No.: 13/177,905

(22) Filed: Jul. 7, 2011

(65) Prior Publication Data

US 2011/0261922 A1    Oct. 27, 2011

Related U.S. Application Data

(62) Division of application No. 12/238,515, filed on Sep. 26, 2008, now Pat. No. 8,036,337.

(30) Foreign Application Priority Data

Oct. 5, 2007   (CN) .......................... 2007 1 0180652

(51) Int. Cl.
*G01N 23/04*    (2006.01)

(52) U.S. Cl. .......................................... 378/57; 378/53
(58) Field of Classification Search .............. 378/50–57, 378/62
See application file for complete search history.

(56) References Cited

U.S. PATENT DOCUMENTS

| 5,132,998 A | 7/1992 | Tsutsui et al. ................. 378/99 |
| 5,182,764 A | 1/1993 | Peschmann et al. ............ 378/57 |

(Continued)

FOREIGN PATENT DOCUMENTS

| CN | 1305610 | 7/2001 |

(Continued)

OTHER PUBLICATIONS

Office Action (with English translation) issued by German Patent Office for corresponding German Application No. 10 2008 050 306. 1, dated Sep. 14, 2011, 10 pgs.

(Continued)

*Primary Examiner* — Courtney Thomas
(74) *Attorney, Agent, or Firm* — Westman, Champlin & Kelly, P.A.

(57) ABSTRACT

Disclosed are a method and a device for security-inspection of liquid articles with dual-energy CT imaging. The method comprises the steps of obtaining one or more CT images including physical attributes of liquid article to be inspected by CT scanning and a dual-energy reconstruction method; acquiring the physical attributes of each liquid article from the CT image; and determining whether the inspected liquid article is dangerous based on the physical attributes. The CT scanning can be implemented by a normal CT scanning technique, or a spiral CT scanning technique. In the normal CT scanning technique, the scan position can be preset, or set by the operator with a DR image, or set by automatic analysis of the DR image.

27 Claims, 16 Drawing Sheets

U.S. PATENT DOCUMENTS

| | | | | |
|---|---|---|---|---|
| 5,367,552 | A | 11/1994 | Peschmann | 378/57 |
| 5,974,111 | A | 10/1999 | Krug et al. | 378/68 |
| 6,026,171 | A | 2/2000 | Hiraoglu et al. | 382/100 |
| 6,078,642 | A | 6/2000 | Simanovsky et al. | 378/57 |
| 6,418,189 | B1 | 7/2002 | Schafer | 378/57 |
| 7,062,011 | B1 | 6/2006 | Tybinkowski et al. | 378/57 |
| 7,116,751 | B2 | 10/2006 | Ellenbogen et al. | 378/57 |
| 7,254,211 | B2 | 8/2007 | Hunt et al. | 378/20 |
| 7,634,061 | B1 | 12/2009 | Turner et al. | 378/98.9 |
| 7,945,017 | B2 * | 5/2011 | Chen et al. | 378/57 |
| 2002/0131634 | A1 | 9/2002 | Weibrecht et al. | 382/162 |
| 2005/0031075 | A1 | 2/2005 | Hopkins et al. | 378/57 |
| 2005/0084063 | A1 | 4/2005 | Heismann et al. | 378/53 |
| 2005/0259781 | A1 | 11/2005 | Ying et al. | 378/5 |
| 2005/0276376 | A1 | 12/2005 | Eilbert | 378/57 |
| 2005/0276468 | A1 | 12/2005 | Ying et al. | 382/154 |
| 2006/0098773 | A1 | 5/2006 | Peschmann | 378/57 |
| 2006/0239402 | A1 | 10/2006 | Hu et al. | 378/54 |
| 2008/0304622 | A1 | 12/2008 | Morton | 378/51 |
| 2009/0092220 | A1 | 4/2009 | Chen et al. | 378/5 |
| 2009/0310744 | A1 | 12/2009 | Petch et al. | 378/53 |

FOREIGN PATENT DOCUMENTS

| | | |
|---|---|---|
| CN | 1319759 | 10/2001 |
| CN | 1779444 | 5/2006 |
| CN | 1916611 | 2/2007 |
| CN | 101071110 | 11/2007 |
| DE | 10 2005 056 385 A1 | 6/2006 |
| DE | 10 2005 056 086 A1 | 7/2006 |
| DE | 20 2005 004 500 U1 | 8/2006 |
| GB | 2420683 | 5/2006 |
| JP | 2004177138 | 6/2004 |
| JP | 2004347328 A | 12/2004 |
| JP | 2005043357 | 2/2005 |
| JP | 2007064727 | 3/2007 |
| JP | 2009014705 | 1/2009 |
| JP | 2009092658 | 4/2009 |
| WO | WO 94/02839 | 2/1994 |

OTHER PUBLICATIONS

Nuclear Instruments & Methods in Physics Research Section A, "Application of X-ray CT to liquid security inspection: System analysis and beam hardening correction," Gao et al., Apr. 2007, pp. 395-399.

EC NDT, "Dual-Energy X-Ray Imaging: Benefits and Limits," Rebuffel et al., 2006, pp. 1-12.

"Combined Search and Examination Report under Sections 17 and 18(3)" for Application No. GB0818056.4 dated Feb. 9, 2009 from Intellectual Property Office, 6 pages.

Search Report from related application PCT/CN2008/001656, dated Jan. 8, 2009, 4 pages.

Office Action from U.S. Appl. No. 12/238,515, mailed Dec. 8, 2010.

Office Action from U.S. Appl. No. 12/240,049, mailed Jul. 28, 2010.

"A New Method of Explosive Detection Based on Dual-Energy X-ray Technology and Forward-Scattering", Nuclear Techniques, vol. 27, No. 10, Oct. 2004,4 pages.

"Application of Dual-Energy DR Method for Material Recognition in CT Image System", Chinese Journal of Stereology and Image Analysis 2007 vol. 12 No. 2 p. 88-92, Jun. 2007, 7 pages.

ScienceDirect, "Application of X-ray CT to Liquid Security Inspection: System Analysis and Beam Hardening Correction", Gao et al., Apr. 1, 2007, 5 pages.

"Quantitative CT Characterization of body fluids with spectral $\rho Z$ projection method" Heismann et al., 2006, prior to Jul. 2011; pp. 2079-2080.

British translation of Chinese Office Action 2007101806528, prior to Jul. 2011; 3 pgs.

Chinese Office Action in Chinese for App. No. 200710180652.8 date Oct. 13, 2010; 13 pages.

Japanese Office Action along with partial English translation of App. No. 2008-259432, mailing date Feb. 1, 2011; 10 pages.

European Search Report for Application No. PCT/CN2008001654 date Dec. 28, 2010; 8 pgs.

English Translation of the Office Action dated May 31, 2011 of the Russian Application No. 2008139276, 5 pages.

Office Action for related Russian Application No. 2008139276, May 31, 2011; 8 pages.

Chinese Office Action issued by SIPO of China for Chinese Application No. 200710180652.8, dated Mar. 31, 2012, 11 pages.

Japanese Office Action issued by JPO for Japanese Application No. 2008-259432, dated Dec. 6, 2011, 4 pages.

English translation for Japanese Office Action issued by JPO for Japanese Application No. 2008-259432, dated Dec. 6, 2011, 3 pages.

* cited by examiner

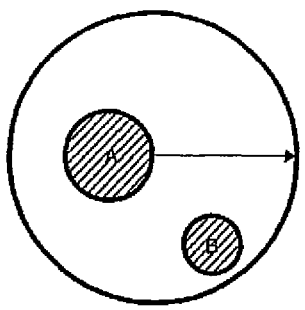
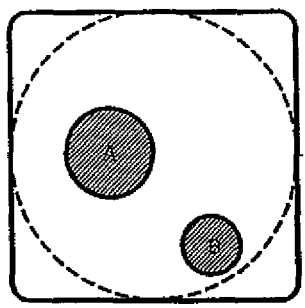
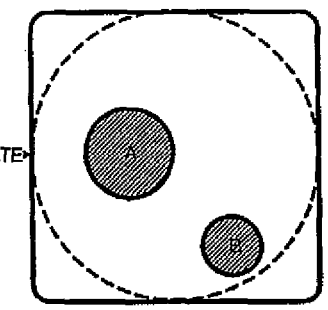
Fig. 16A        Fig. 16B        Fig. 16C
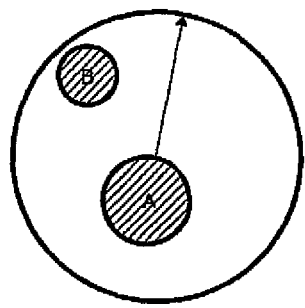
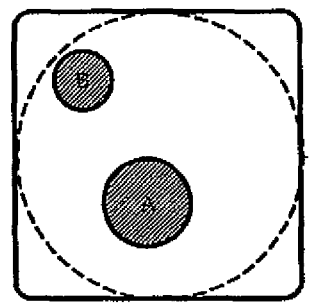
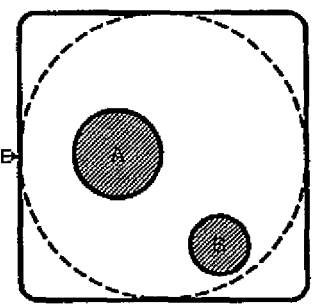
Fig. 16D        Fig. 16E        Fig. 16F
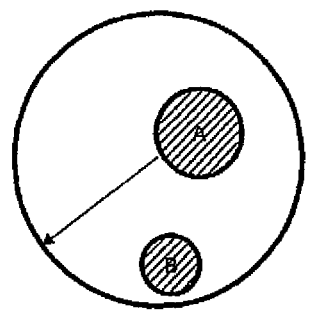
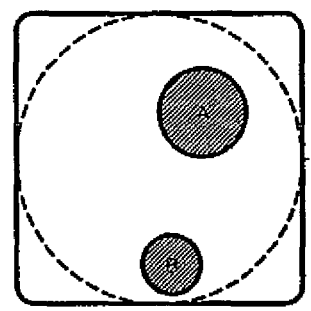
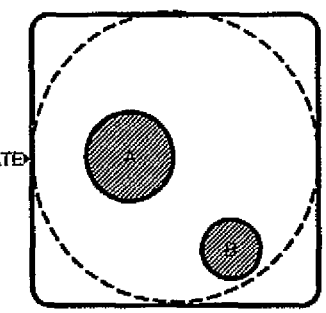
Fig. 16G        Fig. 16H        Fig. 16I
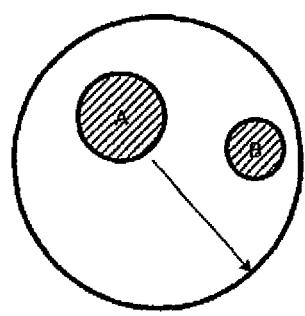
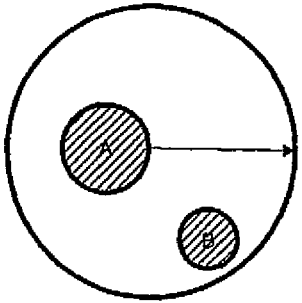
Fig. 16J        Fig. 16K

METHOD AND DEVICE FOR INSPECTION OF LIQUID ARTICLES

CROSS-REFERENCE TO RELATED APPLICATION

The present application is a divisional of and claims priority of U.S. patent application Ser. No. 12/238,515, filed Sep. 26, 2008 now U.S. Pat. No. 8,036,337, which also claims priority of Chinese patent application Serial No. 200710180652.8, filed Oct. 5, 2007, the content of which is hereby incorporated by reference in its entirety.

FIELD OF THE INVENTION

The present invention is related to the field of radiation inspection technique, and more particularly to a method and device for quick security-inspection of liquid articles with dual-energy CT.

BACKGROUND OF THE INVENTION

Since 9•11 in U.S., security-inspection of aviation is becoming more and more emphasized. Besides conventional security-inspection of packages, security-inspection of the liquid articles carried by passengers is added. Accordingly, it is in dire need of means and methods for quick security-inspection of the liquid articles.

Nowadays, there are four types of methods used in security-inspection of liquid articles, including chemical method, electromagnetic method, neutron detection method and radiation detection method as follows:

1) The chemical method can be subdivided into odor identification method, ion scanning explosive detection method and substance analysis method. The odor identification in practical applications often fails to implement detection because of sealed and packaged conditions of liquid articles. The ion scanning explosive detection method is known for its high sensitivity, but with high false alarm rate, it suffers from the affection of background environment. The substance analysis is of high precision and high accuracy, but this method needs a certain period of time to analyze the sample, which cannot meet the demands of on-site quick detection.

2) The electromagnetic method works in an active measurement manner. It distinguishes liquid articles from each other according to their dielectric constants in an electromagnetic field. The electromagnetic method is easily subjected to severe affection of metal packages or other thick material packages. As a result, the use of electromagnetic method is limited in case of complex package materials.

3) The use of the neutron detection method will leave residual radiation remaining in the detected liquid due to the effect of "neutron activation". Furthermore, the radiation shielding is complicate due to neutrons' strong penetrability, and the apparatus has to take a large area, so the method is not suitable for application in the security-inspection systems of civil aviation.

4) Currently, most of the security-inspection apparatuses for civil aviation are radiation apparatuses. In these apparatuses, 2D X-ray imaging technology and three-dimensional CT technology are mostly adopted. These technologies, which are mainly used for security-inspection of packages, fail to accomplish the security-inspection of liquid articles.

The 2D X-ray imaging technology acquires two-dimensional projection images by integrating three-dimensional information of articles along X-ray. These images show internal structures of object in the form of grayscale or pseudo-color, to give the operator a vivid display. However, the 2D X-ray imaging technology is in defect of one-dimensional information of object, so the inspection of liquid articles is suffering from severe affection of shapes and sizes of the liquid articles.

The three-dimensional CT technology is the extension and application of CT technology. The CT technology was applied in the diagnostics first, which was implemented by conducting a multi-angle projection of respective slices of an article. By using a computer to reconstruct the multi-angle projection data of respective slices, reconstructed images were obtained. The information of the different attenuation coefficients in the reconstructed images was displayed in the form of different grayscales, by which the internal structures of the articles were displayed. With the development of the CT technology, the industrial CT for the nondestructive inspection and the package CT for the security-inspection were put into use, with the goal remaining to be acquiring the slice images of the internal structures of articles. It is dependent on human operator's analysis on the structure to determine whether the article is dangerous, and thus is not applicable in automatic and quick inspection. Furthermore, it is difficult for the security-inspection devices of the CT type to gain popularity, for their high cost and bulkiness, as a result of the wide range of the articles that can be detected by them.

To sum up, for the quick detection of the liquid articles, the chemical method, the electromagnetic method and the neutron detection method are not suitable. By using the 2D X-ray imaging technology and the three-dimensional CT technology, images showing the internal structure of the article are acquired, but these images cannot work as sufficient evidence for the automatic security inspection of the liquid articles.

SUMMARY OF THE INVENTION

In order to overcome the disadvantages in the existing technologies, an object of the invention is to provide a method as well as a device for security-inspection of a liquid article using radiations, which can conduct a quick detection and get quantitative information of the liquid article to be inspected, without destroying the outer packing.

In the first aspect of the invention, the invention provides a method for security-inspection of a liquid article with dual-energy CT, comprising the steps of: acquiring dual-energy projection data by dual-energy CT scanning on the liquid article to be inspected; performing CT reconstruction on the projection data to obtain a CT image which indicates physical attributes of the inspected liquid article; extracting the physical attributes of the inspected liquid article based on the CT image; and determining whether the inspected liquid article is dangerous according to the physical attributes.

According to an embodiment of the invention, the physical attributes include the density and atomic number of the liquid article.

According to an embodiment of the invention, the dual-energy CT scanning works in a plane CT scanning manner.

According to an embodiment of the invention, the dual-energy CT scanning works in a normal spiral CT scanning manner.

According to an embodiment of the invention, the dual-energy CT scanning works in a high pitch spiral CT scanning manner.

According to an embodiment of the invention, a set of scan positions are preset prior to the plane CT scanning.

According to an embodiment of the invention, a DR scanning is performed to get a transmission image of the inspected article and the CT scan position is determined based on the transmission image, prior to the plane CT scanning.

According to an embodiment of the invention, after the transmission image has been gotten, the operator specifies at least one row of the transmission image via an input device as the CT scan position.

According to an embodiment of the invention, after the transmission image has been gotten, at least one row of the transmission image is automatically specified by the image processing technique as the CT scan position.

According to an embodiment of the invention, the step of getting the transmission image comprises emitting high-energy radiation beams and low-energy radiation beams which transmit the inspected article to form a high-energy transmission image and a low-energy transmission image; integrating the high-energy transmission image and the low-energy transmission image to form the transmission image.

According to an embodiment of the invention, the step of forming the transmission image comprises emitting high-energy radiation beams and low-energy radiation beams which transmit the inspected article to form a high-energy transmission image and a low-energy transmission image; selecting either the high-energy transmission image or the low-energy transmission image as the transmission image.

According to an embodiment of the invention, the step of performing CT reconstruction on the projection data to obtain a CT image which indicates physical attributes of the inspected liquid article comprises the steps of: generating projection data of two basis material coefficients based on the high-energy and low-energy projection data; performing reconstruction on the projection data of the two basis material coefficients to obtain a CT image which indicates the two basis material coefficients corresponding to the inspected liquid article; and generating a CT image indicating physical attributes of the inspected liquid article based on the CT image indicating the basis material coefficients.

According to an embodiment of the invention, the step of extracting the physical attributes of the inspected liquid article based on the CT image comprises the steps of: extracting pixels corresponding to the liquid article from the CT image; calculating the average density and atomic number of the pixels corresponding to the liquid article as the density and atomic number of the inspected liquid article.

According to an embodiment of the invention, the step of determining whether the inspected liquid article is dangerous according to the physical attributes comprises the steps of: determining whether a point defined by the density and the atomic number falls into a predetermined region in a density-atomic number two-dimensional space; determining that the inspected liquid article is dangerous if the point falls into the predetermined region.

According to an embodiment of the invention, after dual-energy CT scanning at each of the positions, the CT images of the inspected liquid article are rotated to be aligned with the image formed after the first dual-energy CT scanning.

According to an embodiment of the invention, after dual-energy CT scanning at each of the positions, the inspected liquid article is rotated to the position before scanning.

According to an embodiment of the invention, several liquid articles are disposed in a barrel which is divided into multiple subspaces.

According to an embodiment of the invention, the method further comprises steps of: automatically detecting the presence of the barrel with a predefined pattern; determining a certain mark in the CT image in the case of the presence of the barrel; and rotating the barrel to a predefined position based on the certain mark.

According to an embodiment of the invention, the method further comprises the step of displaying determining result of the inspected liquid article on a display screen.

According to an embodiment of the invention, the method further comprises the step of printing determining result of respective liquid articles.

According to an embodiment of the invention, the method further comprises the step of colorizing the CT images of respective liquid articles.

According to an embodiment of the invention, the dual-energy CT scanning is performed on a predetermined position.

In another aspect of the invention, the invention provides a device for security-inspection of a liquid article with dual-energy CT, comprising: a radiation source for emitting radiation beams; detection and collection means for detecting and collecting radiation beams transmitting at least one liquid article to be inspected; a controller for controlling the radiation source and the detection and collection means to perform dual-energy CT scanning on the inspected liquid article so as to obtain projection data; means for performing reconstruction on the projection data to obtain a CT image which indicates physical attributes of the inspected liquid article; and means for determining whether the inspected liquid article is dangerous based on the position of the physical attributes in a corresponding dimensional space.

According to an embodiment of the invention, the dual-energy CT scanning is performed on a predetermined position.

According to an embodiment of the invention, the detection and collection means detects and collects radiation beams transmitting the at least one liquid article to be inspected so as to form a transmission image; wherein the device further comprises means for specifying at least one row of the transmission image; and the dual-energy CT scanning is performed on the specified row.

According to an embodiment of the invention, the physical attributes includes at least the density and atomic number of the inspected liquid article.

According to an embodiment of the invention, the radiation source emits high-energy radiation beams and low-energy radiation beams which transmit the inspected article to form a high-energy transmission image and a low-energy transmission image; and the device further comprises means for integrating the high-energy transmission image and the low-energy transmission image to form the transmission image.

According to an embodiment of the invention, the radiation source emits high-energy radiation beams and low-energy radiation beams which transmit the inspected article to form a high-energy transmission image and a low-energy transmission image; and the device further comprises means for selecting either the high-energy transmission image or the low-energy transmission image as the transmission image.

According to an embodiment of the invention, the means for specifying at least one row of the transmission image comprises means for selecting at least one row by the operator from the transmission image via an input device.

According to an embodiment of the invention, the means for specifying at least one row of the transmission image comprises means for detecting liquid layers in the transmission image by analyzing pixels of the transmission image; and means for specifying central rows of respective layers as the rows to be performed dual-energy CT scanning.

According to an embodiment of the invention, the means for performing reconstruction on the projection data to obtain a CT image which indicates physical attributes of the inspected liquid article comprises means for integrating a density image identified by the density of the inspected liquid article and an atomic number image identified by the atomic number of the inspected liquid article to form a CT image; and means for extracting pixels corresponding to the liquid article from the CT image; and means for calculating the average density and atomic number of the pixels corresponding to the liquid article as the density and atomic number of the inspected liquid article.

According to an embodiment of the invention, the means for determining whether the inspected liquid article is dangerous based on the physical attributes comprises means for determining whether a point defined by the density and the atomic number locates in a predetermined region in a density-atomic number two-dimensional space, wherein the inspected liquid article is determined to be dangerous if the point locates in the predetermined region.

According to an embodiment of the invention, the device further comprises means for, after dual-energy CT scanning at each of the rows, rotating the CT images of the inspected liquid article to be aligned with the image formed after the first dual-energy CT scanning.

According to an embodiment of the invention, the device further comprises means for, after dual-energy CT scanning at each of the rows, rotating the inspected liquid article to the position before scanning.

According to an embodiment of the invention, the device further comprises a barrel which is divided into multiple subspaces for disposing a plurality of liquid articles respectively.

According to an embodiment of the invention, the device further comprises means for automatically detecting the presence of the barrel with a predefined pattern; means for determining a certain mark in the CT image in the case of the presence of the barrel; and means for rotating the barrel to a predefined position based on the certain mark.

According to an embodiment of the invention, the device further comprises display means for displaying determining result of the inspected liquid article.

According to an embodiment of the invention, the device further comprises means for printing determining result of respective liquid articles.

According to an embodiment of the invention, the device further comprises means for colorizing the CT images of respective liquid articles.

According to an embodiment of the invention, the device further comprises a carrier mechanism to carry the liquid articles to be inspected, wherein the surface of the carrier mechanism on which the inspected liquid articles is carried is divided into a plurality of regions the operator can identify.

In yet another aspect of the invention, the invention provides a device for security-inspection of a liquid article with dual-energy CT, comprising a radiation source for emitting radiation beams; detection and collection means for detecting and collecting radiation beams transmitting at least one liquid article to be inspected; a controller for controlling the radiation source and the detection and collection means to perform spiral CT scanning on the inspected liquid article so as to obtain a set of spiral CT images each of which indicates at least one physical attribute of the inspected liquid article; means for analyzing the set of spiral CT images to acquire a spiral CT image part of the liquid article; and means for determining whether the inspected liquid article is dangerous based on the physical attribute contained in the spiral CT image part of the liquid article in a corresponding dimensional space.

With the method and device according to the invention, the transmission image is used as a guide for the dual-energy scanning, and thus the detection speed can be improved without lowing detection accuracy. Furthermore, it can be determined whether the liquid article has an interlayer by means of the transmission image.

Besides, it can be determined whether the liquid article is an explosive based on whether the measured density and atomic number locate in a predetermined region in a two-dimensional space.

In addition, inspection operation is facilitated because the operator can specify any position to perform the dual-energy CT scanning.

Further, a divided barrel is used when a plurality of articles is to be inspected, and so it can be easily determined which one of the liquid articles is dangerous.

BRIEF DESCRIPTION OF THE DRAWINGS

The features and advantages of the invention can be more apparent from the following detailed descriptions with reference to the accompanying drawings in which.

FIG. 16A to FIG. 16K show a process how to rotate the CT reconstruction images and/or the carrier mechanism to be aligned with the position before CT scanning;

DETAILED DESCRIPTION OF THE PREFERRED EMBODIMENTS

Figure 1:
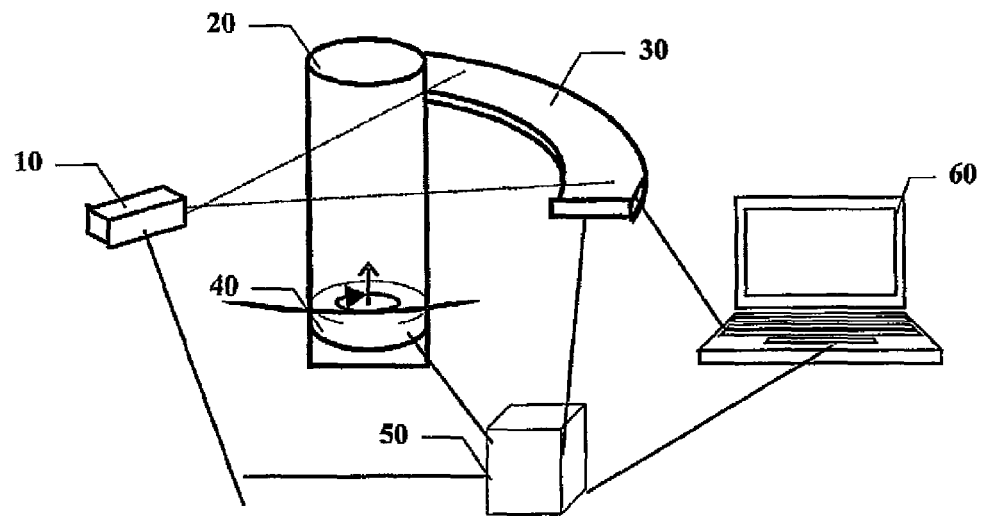
FIG. 1 is a schematic diagram of an inspection device according to an embodiment of the present invention.

The preferred embodiments of the invention will now be described more fully hereinafter with reference to the accompanying drawings. In the drawings the same reference numerals are used for denoting the same or similar components that are shown in different figures. For clarity, the detailed description of the known function and structure incorporated herein will be omitted, which would otherwise weaken the subject of the invention.

First Embodiment

FIG. 1 is a schematic diagram of the structure of an inspection device according to an embodiment of the invention.

As shown in FIG. 1, the inspection device according to the invention comprises a radiation source 10 for emitting dual-energy X-rays for inspection, e.g. a X-ray machine; a carrier mechanism 40 which carries the liquid article 20 to be inspected and can rotate around axis Z thereof and can ascend or descend to take the liquid article 20 into the inspection area, thereby the radiations emitted by the radiation source 10 can transmit through the inspected liquid article 20; a detection and collection means 30 being an integrated module of a detector and a data collector, which is used to detect the dual-energy radiations transmitted through the liquid article 20 to acquire analog signals, and convert the analog signals into digital signals, and hence output the scanning data of the liquid article 20 with respect to the high energy X-rays and low energy X-rays; a controller 50 which controls each component of whole system so that they operate synchronously; and a computer data processor 60 for processing the data collected by the data collector and outputting inspection results.

As shown in FIG. 1, the radiation source 10 is placed at one side of the carrier mechanism 40 carrying the liquid article 20 to be inspected, while the detection and collection means 30 is placed at the other side of the carrier mechanism 40. The detection and collection means 30 comprises a detector and a data collector for acquiring the DR data and the multi-angle projection data of the liquid article 20. The data collector has a signal amplifying and shaping circuit, which operates under (current) integration mode or pulses (counting) mode. The detection and collection means 30 has its data output cable connected with the computer data processor 60 to store the collected data into the computer data processor 60 according to trigger instructions.

Besides, the inspection device also comprises a cylindrical article passage 20 made of metals and having openings at lower portions of side wall to allow the liquid article can be irradiated by radiations and shield some of the radiations that do not irradiate the liquid articles. The inspected liquid article 20 is placed in the article passage.

Figure 2:
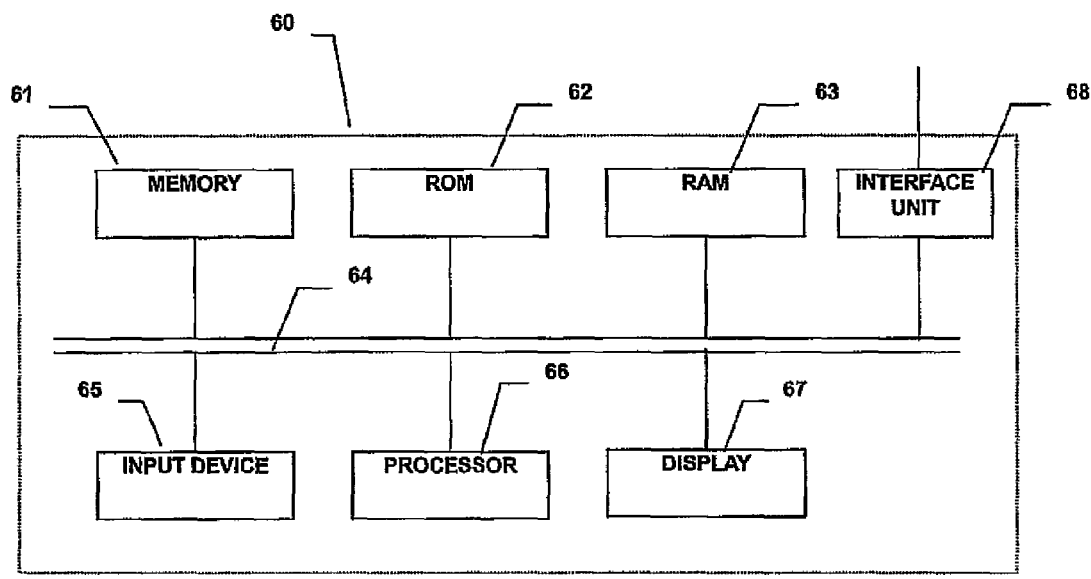
FIG. 2 shows a block diagram of the computer data processor 60 in the inspection device of FIG. 1.

FIG. 2 shows a block diagram of the computer data processor 60 of FIG. 1. As shown in FIG. 2, the data collected by the data collector are stored in the memory 61 through an interface unit 68 and a bus 64. The configuration data and programs of the computer data processor are stored in the ROM (Read Only Memory) 62. The RAM (Random Access Memory) 63 is used for temporarily storing various data during the operating procedure of the processor 66. Besides, computer programs are also stored in the memory 61 for data processing. The internal bus 64 connects the memory 61, the ROM 62, the RAM 63, the input device 65, the processor 66, the display device 67 and the interface unit 68 together.

After the user inputs operation commands through the input device 65 such as keyboards and mouse, the instruction code of the computer programs will instruct the processor 66 to perform a predetermined data processing algorithm. After the processing results are obtained, they will be displayed on the display device 67 such as a LCD, or redirected in the form of a hard copy such as printing.

Figure 3:
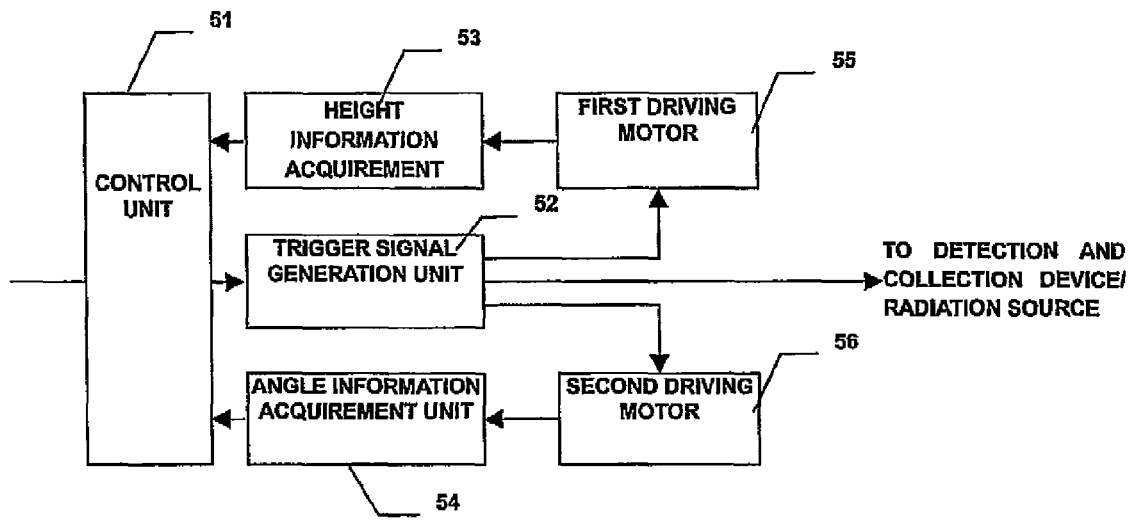
FIG. 3 shows a block diagram of the controller according to a first embodiment of the present invention.

FIG. 3 shows a block diagram of the controller according to a first embodiment of the invention. As shown in FIG. 3, the controller 50 comprises a control unit 51 for controlling the radiation source 10, the carrier mechanism 40 and the detection and collection means 30 based on instructions from the computer 60; a trigger signal generation unit 52 for generating trigger commands for triggering the radiation source 10, the detection and collection means 30 and the carrier mechanism 40 to operate under the control of the control unit 51; a first driving motor 55 for driving the carrier mechanism 40 to ascend or descend according to the trigger command generated by the trigger signal generation unit 52 under the control of the control unit 51; a height information acquirement unit 53 for feeding the height information of the carrier mechanism back to the control unit 51 as the carrier mechanism movies; an angle information acquirement unit 54 for feeding the rotation angle of the carrier mechanism 40 back to the control unit 51 during the rotation process of the carrier mechanism 40.

According to the embodiment of the invention, the height information acquirement unit 53 and the angle information acquirement unit 54 both are photoelectrical coded discs, and thus they have the advantage of anti-interference.

According to the embodiment of the invention, dangerous articles can be inspected by measuring the density and atomic number of the liquid in the liquid articles and determining whether the measured density and atomic number fall into a predetermined danger region. The density and atomic number of secure liquid (such as drinks, skin care products, cosmetic, etc.) and those of dangerous liquid (such flammable liquid, liquid explosive, strong corrosive liquid, etc.) are dramatically different from each other. For example, as to the water which is secure liquid, the density thereof is about 1 (its characteristic density is 1.11), and the atomic number thereof is about 7.51. As to the alcohol which is dangerous liquid, the density thereof is about 0.79 (its characteristic density is 0.89), and the atomic number thereof is about 6.47. Therefore, the secure liquid and the dangerous liquid can be distinguished from each other based on the density and atomic number by a pattern recognition method.

Figure 4:
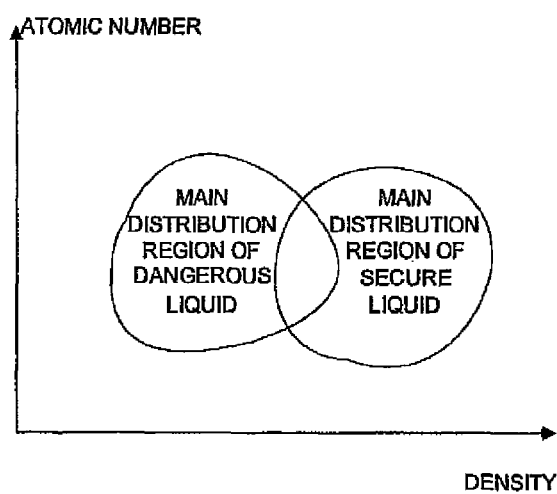
FIG. 4A and FIG. 4B show diagrams of the liquid article inspection method according to the present invention.
Figure 4B:
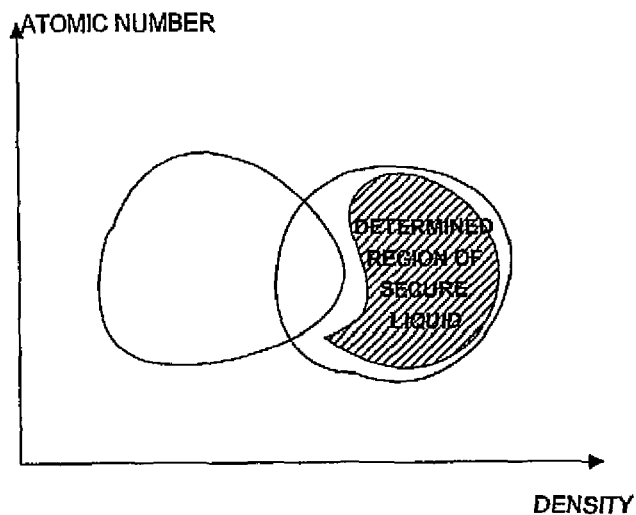

FIG. 4A and FIG. 4B show diagrams of the liquid article inspection method according to an embodiment of the present invention. In the two-dimensional space constructed by density and atomic number, one or more regions are identified such that if the density and atomic number of the inspected article locate at these regions, then the inspected article is considered as secure liquid; otherwise it is considered as dangerous liquid. The regions for secure liquid are determined by measuring a large number of secure liquid and dangerous liquid, and taking the regions where the secure liquid is dense whereas the dangerous liquid is sparse as the regions for secure liquid. As shown in FIG. 4A, a region for secure liquid and a region for dangerous liquid can be determined in the density-atomic number two-dimensional space by measuring the density and atomic number of various liquid. Then, the region for secure liquid shrinks to improve the inspection sensitivity, as shown in FIG. 4B. In such a way, having obtained the density and atomic number of the liquid article, it can be determined whether the liquid article is dangerous based on position of the density and atomic number in the two-dimensional space.

Figure 5:
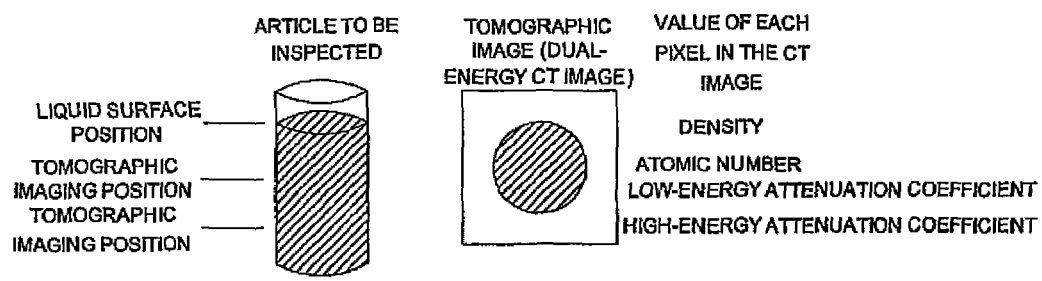
FIG. 5 is a diagram showing the relationship between a DR imaging and a CT imaging.

FIG. 5 is a diagram showing the relationship between a DR imaging and a CT imaging. According to the embodiment of the invention, a DR imaging is firstly performed on the liquid article to determine the liquid portion of the liquid article, and then a CT imaging is performed on the liquid portion only so as to improve the inspection speed.

Figure 6:
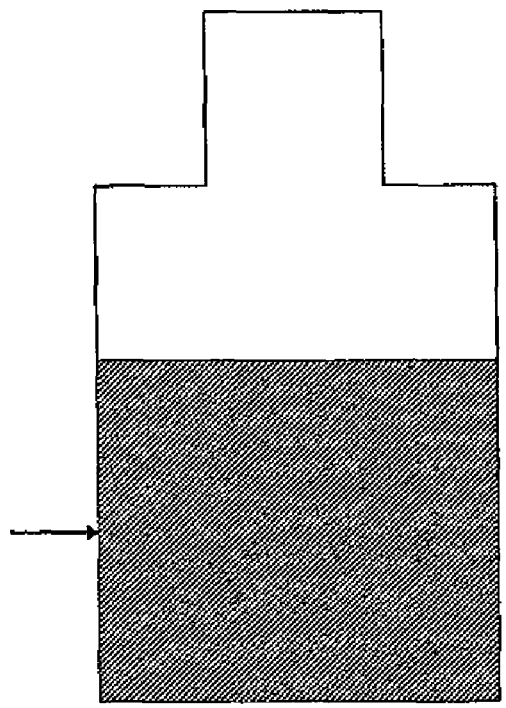
FIG. 6 shows an example of the result of the DR imaging.
Figure 7:
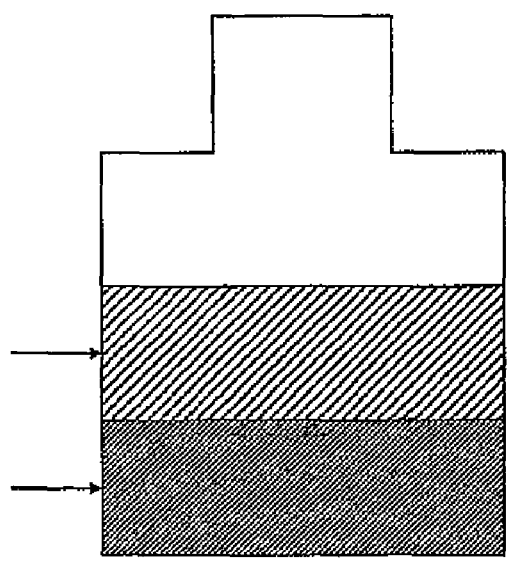
FIG. 7 shows another example of the result of the DR imaging.

FIG. 6 and FIG. 7 show examples of the result of a DR imaging, respectively. As shown in FIG. 6, after a DR imaging is performed on a liquid article, the liquid in the liquid article can be determined by analysis of pixels as described below. As shown in FIG. 6, the liquid article only contains a kind of liquid. However, as shown in FIG. 7, due to different attenuation coefficients of different kinds of liquid, when two or more kinds of liquid are contained in the liquid article and form several layers, the positions of the layer interfaces can be determined by analysis of pixels of the DR image obtained through a DR imaging. After that, CT imaging can be performed one by one on each layer of liquid.

Figure 8:
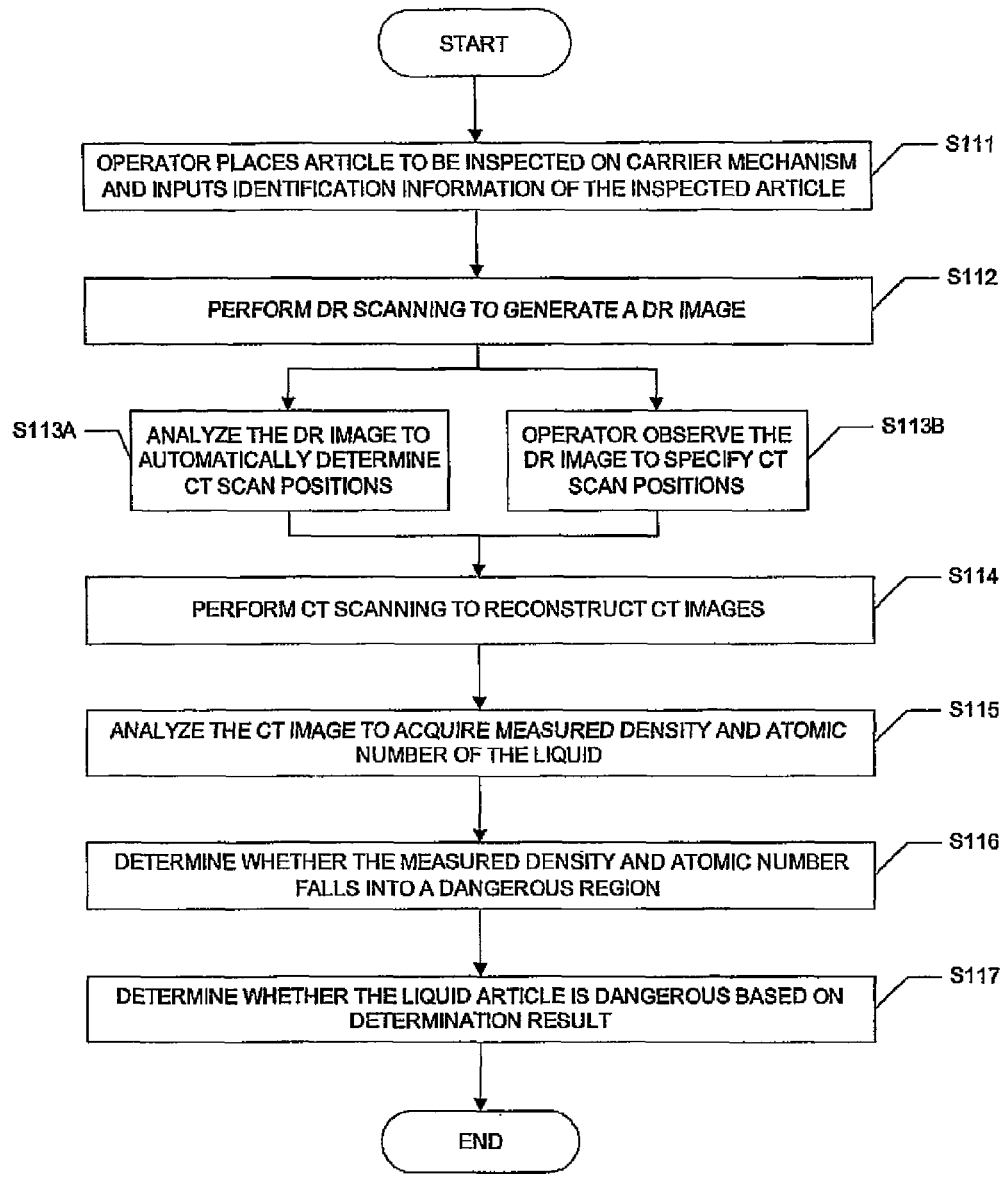
FIG. 8 shows an outline flowchart of the liquid article inspection method according to the first embodiment of the invention.

FIG. 8 shows an outline flowchart of the liquid article inspection method according to the first embodiment of the invention. As shown in FIG. 8, liquid articles carried by a passenger should pass through security-inspection, for example, when he/she passes the customs. Firstly at step S111, the human operator places the liquid article to be inspected on the carrier mechanism 40.

Next, at step S112, the operator presses a start bottom to start a DR scanning so as to generate a DR image, as shown in FIG. 6 and FIG. 7.

As described above, the purpose of DR scanning is to acquire a transmission image of the inspected liquid articles so that the operator can discern the internal structure of the inspected liquid articles to specify positions in the DR image where CT imaging should be performed. The system software can also use the DR image to automatically identify the positions of the liquid layers and guide the following CT imaging. The detailed process of the DR imaging will be described below.

What should be noted is that the DR scanning is optional. The CT scanning can be performed by directly specifying several positions without guidance of the DR scanning, to improve the inspection speed. For example, it is found that most liquid articles have at least 5 cm of liquid in height; so 5 cm from the bottom can be used as a pre-specified scan position. Furthermore, the operator can visually detect the size of the inspected article, and specifies a proper height experientially. For example, the scan height of canned Coca Cola can be set as 3 cm, while the scan height of a bottle of wine with a thick bottom can be set as 10 cm.

Having obtained the DR image, the CT scan positions can be determined either by automatic analysis of the DR image (step S113A), or by the operator using the input device 65 such as a mouse (step S113B), or by a mixture of both methods. In such a way, CT scanning is only performed at certain positions in the liquid articles, so that the inspection is speeded up without lowering the inspection quality.

Then CT scanning process is performed at step S114 at the determined positions in the liquid articles to obtain CT projection data and CT image are reconstructed based on the CT projection data. Each pixel of the CT image denotes the density, atomic number and other physical attributes of corresponding portion in the liquid articles.

Next, the computer analyzes the CT image by executing an analysis program, and obtains the measured density and atomic number at step S115. Then, at step S116, it is determined whether a point defined by the measured density and atomic number locates in a predetermined region in the density-atomic number two-dimensional space. At step S117, if the point defined by the density and atomic number locates in the predetermined danger region, then the liquid article is suspicious and might be a dangerous article, and the operator is alarmed or the inspection result is printed.

Figure 9:
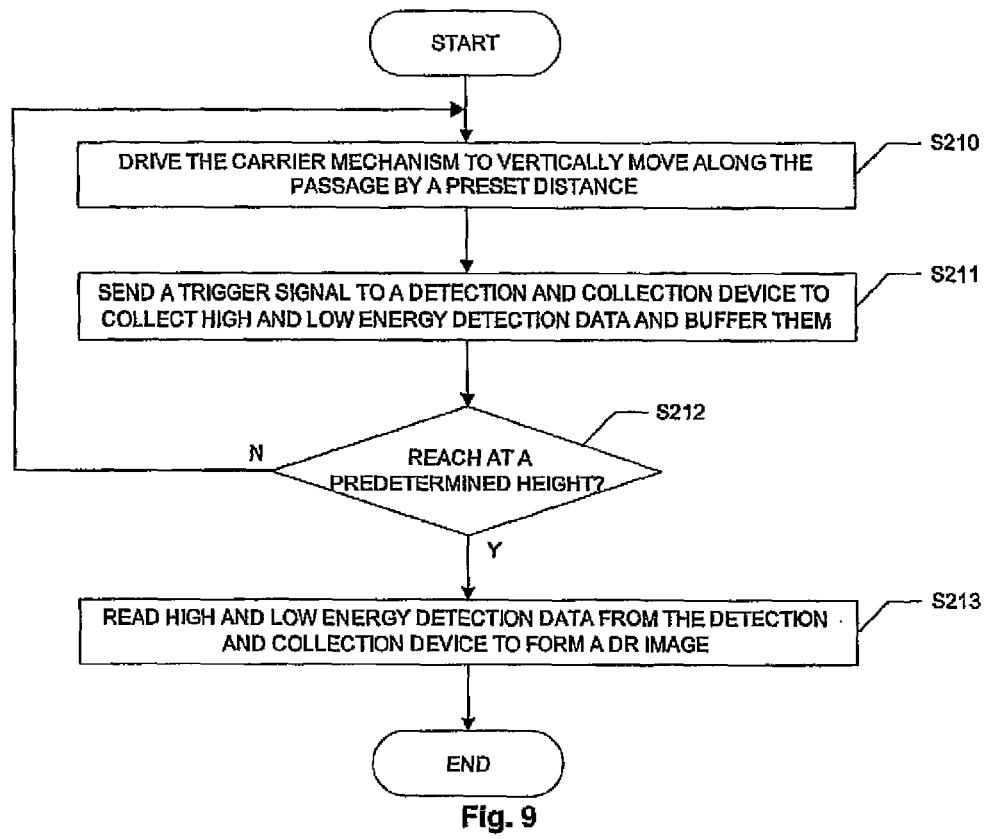
FIG. 9 shows a flowchart of the process of a DR imaging.
Figure 10:
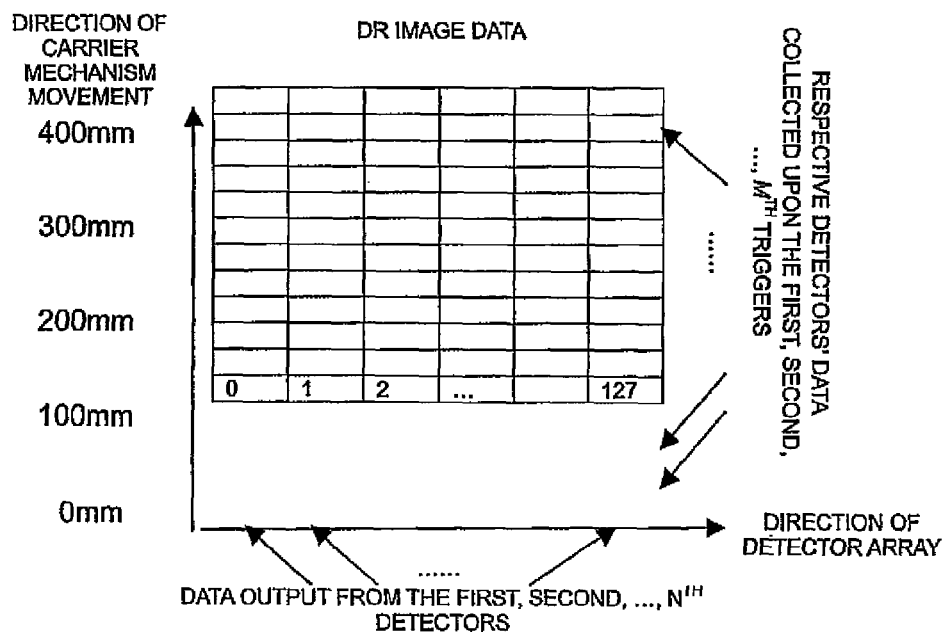
FIG. 10 shows an arrangement of the DR image data collected by the detection and collection device 30 during the process of the DR imaging.

Detailed operation of each step will be described with respect to FIGS. 9-14. FIG. 9 shows a flowchart of the process of a DR imaging, and FIG. 10 shows the arrangement of the DR image data collected by the detection and collection means 30 during the process of the DR imaging.

As shown in FIG. 9, during the DR imaging, at step S210, a command is sent to the controller 50 from the computer 60 to drive the carrier mechanism 40 to vertically move along the article passage 20. The controller 50 monitors the height of the carrier mechanism in real time through the height information acquirement unit 53 as the carrier mechanism vertically moves.

At step S211, the controller 50 sends a trigger signal to the detection and collection means 30 at intervals of a certain height (for example, 1 mm) The detection and collection means 30 receives the trigger signal, and then collects output signals from each detector to obtain high-energy detection data and low-energy detection data, and save them in its internal buffer.

At step S212, it is determined whether the carrier mechanism 40 reaches at a specified height or not, such as 500 mm. If not, then the flow proceeds to step S210.

If the carrier mechanism 40 reaches at the specified height, then the controller 50 will not send the trigger signal to the detection and collection means 30. The computer 60 reads collected high and low energy detection data from the detection and collection means 30, and arranges them in a matrix to form a DR image. Each pixel of the DR image records the residual intensity of the radiations after transmitting through the article, including low-energy radiation intensity and high-energy radiation intensity.

As described above, the CT scan positions are determined based on the DR image. By either automatic identification or manual specification, a row id in the DR image is obtained firstly, and then the id is converted to the height of the carrier mechanism by the computer, and the controller 50 is instructed to drive the carrier mechanism 40 to a specified position, and then a CT imaging is performed.

From the flowchart of the DR imaging, each row of the DR image corresponds to a height of the carrier mechanism 40. If it is assumed that the height of the carrier mechanism is 0 when the DR imaging starts, the carrier mechanism 40 descends during the imaging, and collection is trigged at intervals of h mm, then the $m^{th}$ row in the DR image corresponds to a height of $-m*h$ of the carrier mechanism.

Figure 11:
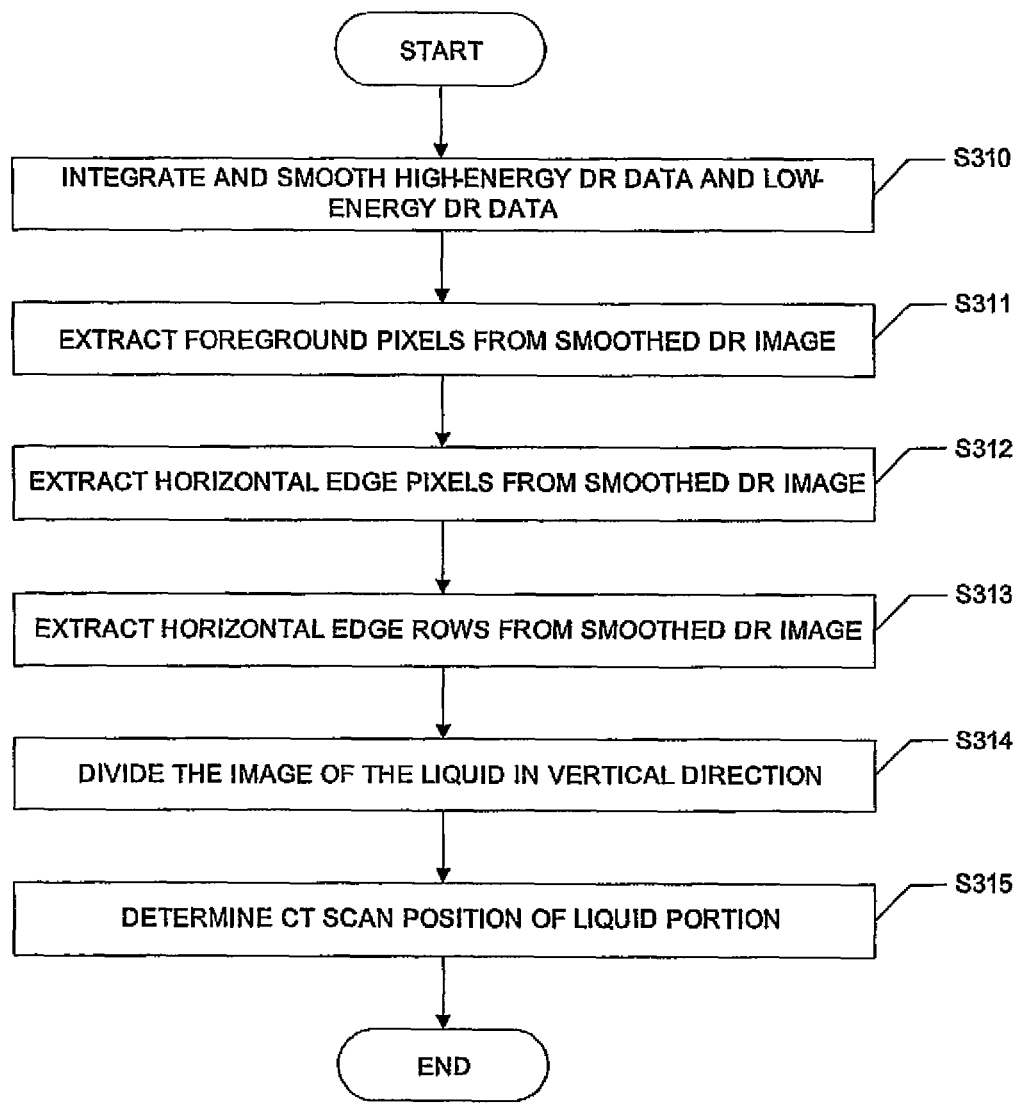
FIG. 11 shows a flowchart of a process of determining a CT scan position by processing DR image.

FIG. 11 shows a flowchart of a process of determining a CT scan position by processing on the DR image.

In the DR image, the inspected liquid article is generally divided into a bottle bottom, a liquid portion, a bottle neck, a bottle cover and so on. The liquid portion can be extracted by an image analysis technique, and then the CT scan positions can be determined.

At step S310, a single-value DR image with low noise can be obtained by integrating and smoothing the high and low energy data of the DR image. For example, the specific method for integrating the high and low energy data can be selection of either the high or low energy data as the integration result, or weighted combination of the high and low energy data. The smoothing method can be a filtering process of the image with a Gauss filter.

At step S311, the liquid article (foreground) in the smoothed DR image is extracted, and the air (background) is removed. The specific method can set a threshold, and take pixels with values above the threshold as foreground pixels, and other pixels as background pixels. The principle of using a threshold to remove the background is that the liquid article blocks the radiations, and thus the corresponding pixels in the DR image have low values (the DR image records the residual intensity of the radiations).

At step S312, horizontal edge pixels in the smoothed DR image are extracted. The specific method is to calculate the difference between each pixel in the DR image and an adjacent pixel next in vertical direction, and take the pixel as the horizontal edge pixel if the difference is larger than a threshold.

At step S313, horizontal edge rows in the smoothed DR image are extracted. The horizontal edge rows are corresponding to the interface between the bottom and the liquid, the interface between the liquid and the air, and the interface between the cover and the air or interfaces in the container between different liquid layers. The method to get the horizontal edge rows is to calculate a ratio of the number of the horizontal edge pixels and the number of foreground pixels on each row, and take the row as the horizontal edge row if the ratio is larger than a threshold (for example, 50%).

At step S314, the DR image is divided vertically, and non-liquid regions are excluded. Horizontal edge rows in the DR image divide the DR image into a number of regions, including a bottle bottom, a liquid portion (may have several layers in different densities), a spacing portion inside the bottle (if any) and a bottle cover. The non-liquid regions can be excluded by establishing a choosing rule, which can be:

a) In the vertical direction, a region with the number of rows lower than a threshold is excluded. The region with a low number of rows is a region of little thickness, which might be the bottle bottom, the bottle cover or a spacing portion in the top of the bottle (for example, the air at the top of a can). The threshold can be set by investigating the bottle bottom, the bottle cover and the thickness of the air in the container of various containers of liquid packs.

b) In the horizontal direction, a region with average foreground pixel number of every row lower than a threshold is excluded. Such a region generally is the slender bottle neck. The threshold can be set by acquiring the width of the bottle necks of various containers of liquid packing.

At step S315, the CT scan position of the liquid region(s) is determined to locate respective layers of the liquid, excluding the non-liquid regions. The central rows in the height direction of these regions are taken as the CT scan positions.

Above described is the process for automatically determining the CT scan positions. In the case of manually specifying the scan positions, the operator directly specifies rows on the displayed DR image via the input device 65 as the CT scan positions.

Figure 12:
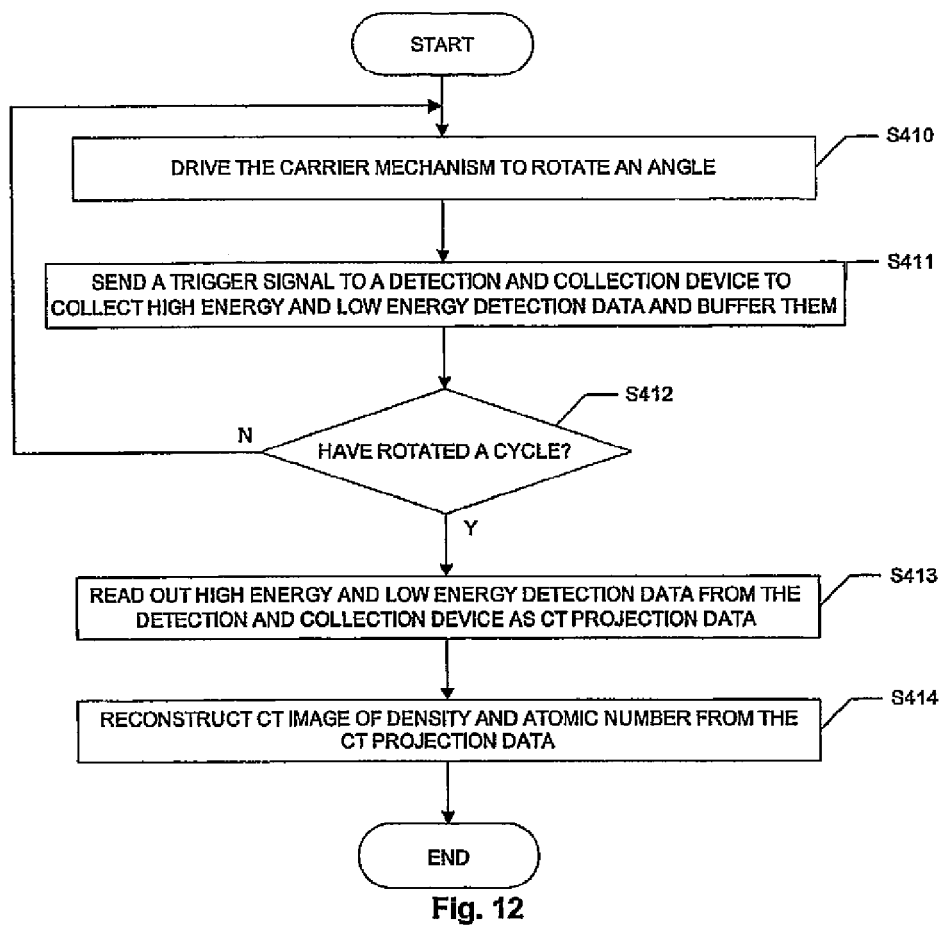
FIG. 12 shows a process for CT imaging.
Figure 13:
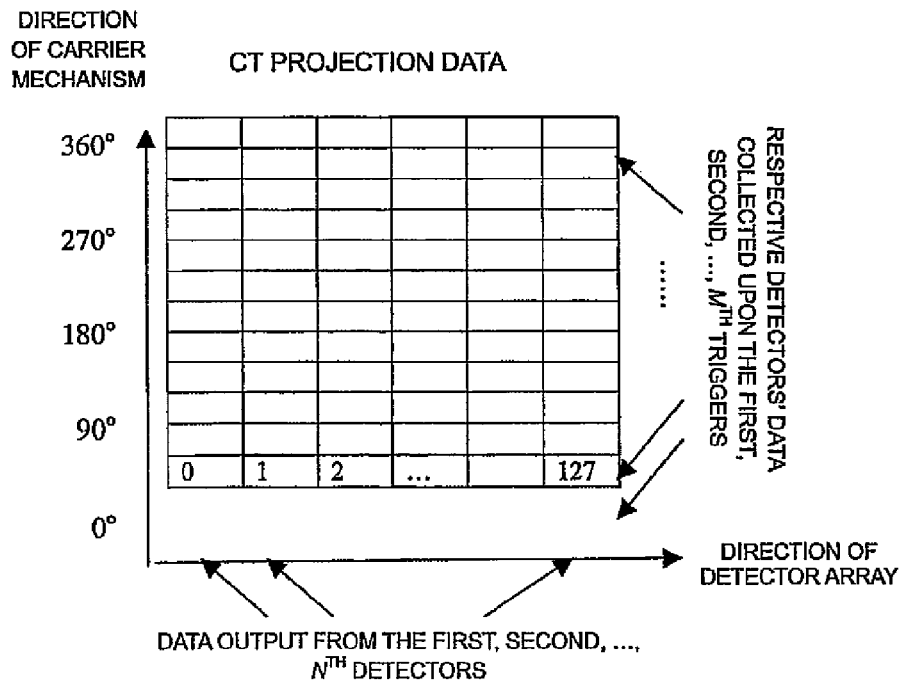
FIG. 13 shows an arrangement of the CT projection data during the process of the CT imaging.

FIG. 12 shows a process of a CT imaging, and FIG. 13 shows the arrangement of the CT projection data during the process of the CT imaging.

As shown in FIG. 12, after the CT positions have been determined, a CT imaging process is performed, i.e. a CT imaging is performed at the determined CT scan positions to generate a density-atomic number image of one slice of the inspected article, to measure the density and atomic number of the liquid. As described above, the CT imaging is only performed on the typical positions, and thus the passing time can be largely saved.

At step S410, the computer 60 sends a command to the controller 50 to drive the carrier mechanism 40 to rotate an angle, such as one degree. The controller 50 monitors the angle of the carrier mechanism in real time via the angle information acquirement unit 54 during the carrier mechanism rotates.

At step S411, the monitor 50 sends a trigger signal to the detection and collection means 30 after a rotation of one degree. The detection and collection means 30 receives the trigger signal, and collects output signals of respective detectors and saves them in its internal buffer.

Next, at step S412, it is determined whether cumulated rotation angle reaches a cycle or not. If not, then the flow proceeds to step S410 and continues the above process.

If the cumulated rotation angle reaches a specified angle (such as 360 degrees), then at step S413, the rotation ceases, and the controller 50 will not send a trigger signal to the detection and collection means 30 any more. The computer 60 reads out collected high and low energy detector signals from the detection and collection means 30 and arranges them in a data matrix to form CT projection data, as shown in FIG. 13. Each pixel of the CT projection data records the residual intensity of the radiations after transmitting through the article, including the low energy radiation intensity and the high energy radiation intensity.

At step S414, the computer 60 reconstructs a tomographic image of the density and atomic number, i.e. a CT image, from the high and low energy CT projection data by a dual-energy reconstruction algorithm. Each pixel of the CT image records the density and atomic number of the inspected article at the position corresponding to the pixel.

The process of reconstructing tomographic image from the high and low CR projection data will be described below.

Mathematical Principle of CT

A one-dimensional function $p_\theta(t)$ can be obtained by linearly integrating a two-dimensional distribution $u(x,y)$ along a direction $\theta$, which function is referred to as the projection of $u(x,y)$ at an angle $\theta$. If $p_\theta(t)$ of respective directions have been obtained, then the two-dimensional distribution $u(x,y)$ can be accurately calculated through a Radon transform. The process of calculating a two-dimensional distribution from projection is referred to as reconstruction.

In real application, projection of attenuation coefficient of a slice of an article in respective directions can be measured by an X-ray machine and a detector rotating around the article a cycle. Then the two-dimensional distribution of the attenuation coefficient can be reconstructed from the CT principle.

Basis Material Decomposing Model

In the energy range of a mini X-ray security inspection system (<200 keV), the attenuation coefficient of radiation can be approximately expressed as following formula (I).

$$\mu(E) = a_1 f_P(E) + a_2 f_{KN}(E) \quad (1)$$

$$a_1 = \frac{\rho Z}{M} Z^n \quad (2)$$

$$a_2 = \frac{\rho Z}{M} \quad (3)$$

In formula (I), the linear attenuation coefficient, $\mu(E)$, as a function of X-ray energy E, is decomposed to $f_p(E)$, which demotes the contribution from photoelectric effect, and $f_{KN}$ (E), the Compton effect. Both $f_p(E)$ and $f_{KN}(E)$ have known formulas, which are omitted here. The decomposition coefficients $a_1$ and $a_2$ are related to the atomic number, mass number and density, with formulas being shown in (2) and (3), in which Z denotes the atomic number, M denotes the mass number, $\rho$ denotes the density (g/cm³) and n is a constant.

According to formula (I), with a given X-ray energy distribution, the linear attenuation coefficient of each substance can be uniquely determined by only two coefficients $a_1$ and $a_2$. Therefore, if we select two basis materials, such as carbon and aluminum, then and all other materials can be expressed as the linear combination of the line attenuation coefficients of these basis materials, as shown in the following formula (4).

$$\mu(E) = b_1\mu_1(E) + b_2\mu_2(E) \quad (4)$$

Formula (4) is just a linear transformation of formula (I), wherein $\mu_1(E)$ and $\mu_2(E)$ are the linear attenuation coefficients of the selected basis materials, and $b_1$ and $b_2$ are called basis material coefficients. Another interpretation of formula (4) is that the linear attenuation coefficient of any material can be regarded as a weighted sum of the linear attenuation coefficients of two basis materials.

Then we define a characteristic density, $\rho^*$, as the product of the ratio of double atomic number and the mass number with the density, as in formula (5).

$$\rho^* = \rho \frac{2Z}{M} \quad (5)$$

Assume that the atomic numbers and characteristic densities of the two basis materials are already known as $(Z_1, \rho_1^*)$ and $(Z_2, \rho_2^*)$ respectively, the atomic number and characteristic density of any material can be derived from the above formulas (1)~(4) as follows.

$$\rho^* = b_1\rho_1^* + b_2\rho_2^* \quad (6)$$

$$Z = \left(\frac{b_1\rho_1^* Z_1^n + b_2\rho_2^* Z_2^n}{b_1\rho_1^* + b_2\rho_2^*}\right)^{1/n} \quad (7)$$

Basis Material Projection Model

The energy spectrum generated by an X-ray tube is typically a continuous spectrum. The energy response function of a detector to X-rays is not constant. Assume that the product of the energy spectrum N(E) and the energy response function $P_d(E)$ is S(E), and S(E) is normalized as follows, $$\int_0^{E_m} S(E) dE = 1 \quad (8)$$

then the projection on a projection line can be expressed as following integration:

$$p = -\ln\frac{I}{I_0} = -\ln\int_0^{E_m} S(E)\exp\left(-\int_l \mu(E, x, y) dl\right) dE \quad (9)$$

in which $I_0$ and I respectively denote the detector readings before and after the radiations are attenuated by the article, $E_m$ denotes the maximum energy of the radiations, and l denotes the path of the radiations.

The above formula (9) shows the relationship between the measured projection p and the two-dimensional distribution $\mu(x, y)$. It is obvious that the formula (9) is not the linear integration of $\mu(x, y)$ because the X-ray energy is not a const, and thus does not meet the requirement of the mathematical principle of CT.

The conventional reconstruction algorithm neglects such uniformity, as a result the reconstructed image of $\mu(x, y)$ will have an artifact of a cup shape, which is called hardened artifact. If we calculate two sets of $\mu(x, y)$ by conventional reconstruction algorithm, and then derive information such as the atomic number and density, the result will also have artifacts.

The present invention solves this problem with basis material decomposition model. Substituting formula (4) in formula (9), we will get a basis material projection model, $$p = -\ln\int_0^{E_m} S(E)\exp\left(-\int_l [\mu_1(E) b_1(x, y) + \mu_2(E) b_2(x, y)] dl\right) dE \quad (10)$$

Let $$\int_l b_1(x,y) dl = B_1 \quad (11)$$

$$\int_l b_2(x,y) dl = B_2 \quad (12)$$

in which $B_1$ and $B_2$ are referred to as the projection of the basis material coefficients $b_1(x, y)$ and $b_2(x, y)$. Then the dual-energy projection data as follows can be obtained by collecting the projection data in dual-energy.

$$p_1(B_1, B_2) = -\ln\int_0^{E_1} S_1(E)\exp[-B_1\mu_1(E) - B_2\mu_2(E)] dE \quad (13)$$

$$p_2(B_1, B_2) = -\ln\int_0^{E_2} S_2(E)\exp[-B_1\mu_1(E) - B_2\mu_2(E)] dE \quad (14)$$

in which $E_1$ denotes the maximum energy of the low-energy radiations, and $E_2$ denotes the maximum energy of the high-energy radiations. After $(p_1, p_2)$ is measured, $(B_1, B_2)$ can be solved based on the formulas (13) and (14), which will be described in the next section. And after $(B_1, B_2)$ in all angles have been obtained, the distribution of the basis material coefficients $b_1(x,y)$ and $b_2(x,y)$ can be reconstructed according to the CT reconstruction theory. Then the atomic number and characteristic density distribution of the article and the linear attenuation coefficient of any energy can be calculated according to the basis material decomposition model.

Solution of Basis Material Coefficient Projection $(B_1, B_2)$

Both formulas (13) and (14) are logarithmic integral formulas, which can not be resolved analytically. The conventional non-linear iterative method needs a great deal of calculation, and can not easily obtain stable solutions.

It should be noted that the measured dual-energy projection can be expressed as follows after the radiations pass through the basis materials 1 and 2 with thickness of $d_1$ and $d_2$:

$$p_1 = -\ln\int_0^{E_1} S_1(E)\exp[-d_1\mu_1(E) - d_2\mu_2(E)] dE \quad (15)$$

$$p_2 = -\ln\int_0^{E_2} S_2(E)\exp[-d_1\mu_1(E) - d_2\mu_2(E)] dE \quad (16)$$

Comparing formulas (13) and (14) with (15) and (16), it can be seen that the measured projection pair ($p_1$, $p_2$) is the same. That is, the projection data pair ($B_1$, $B_2$) of the basis materials is just the same as the thickness pair ($d_1$, $d_2$) of the basis materials. Therefore, the correspondence between the dual-energy projection data pair ($p_1$, $p_2$) and the basis material coefficient projection data pair ($B_1$, $B_2$) can be obtained by measuring the dual-energy projection of different thickness pair, and a look-up table can be formed. A pair ($B_1$, $B_2$) can be calculated from ($p_1$, $p_2$) according to the look-up table by linear interpolation, instead of a complex solution process.

Figure 14:
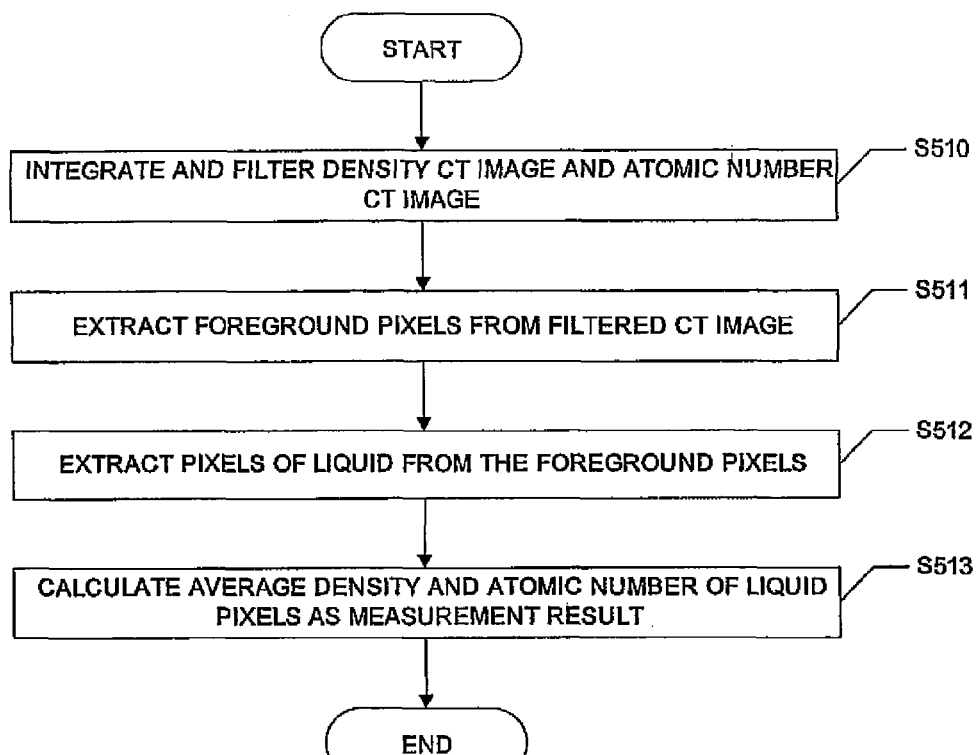
FIG. 14 shows a process for measuring the attributes of the liquid.

FIG. 14 shows the process for measuring the attributes of the liquid.

As shown in FIG. 14, at step S510, the density image and the atomic number image are integrated and smoothed to form a single value CT image with low noise. The specific integration method can be selection of either the density image or the atomic number image as the integration result, or weighted combination of both images. The specific smoothing method can be filtering the image with a Gauss filter.

At step S511, the inspected articles (foreground, including the liquid and the pack thereof) in the smoothed CT image is extracted, and the air image (background) is removed. A specific method is to set a threshold, and take pixels with values above the threshold as foreground pixels, and other pixels as background pixels. The reason is that the density and atomic number of air are nearly zero, whereas those of the inspected liquid article are relatively larger.

At step S512, the liquid pixels in the foreground pixels are extracted. A specific method for extraction may include the following steps. Firstly, it establishes a binary image corresponding to the CT image, setting the value of the foreground pixels to one, the value of the background pixels to zero. Then the morphological erosion technique is applied to binary image to remove the packing, since the liquid is always inside the packing. The times of corrosions can be set in accordance with the thickness of the packing.

At step S513, the average density and average atomic number of all the liquid pixels in the CT image can be calculated as the output result of this measurement.

Furthermore, if the DR image analysis process finds that the liquid has multiple layers, the above steps are repeated with respect to each layer to determine if any layer is suspicious. The operator can be informed of the final inspection result.

Second Embodiment

Figure 15A:
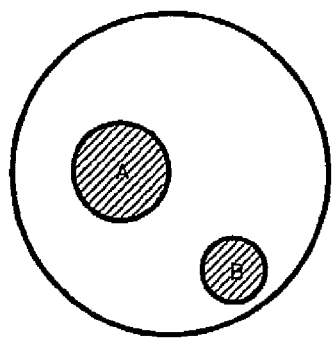
FIG. 15A and FIG. 15B show diagrams of CT images reconstructed in the case that there are several liquid articles to be inspected according to a second embodiment of the present invention.
Figure 15B:
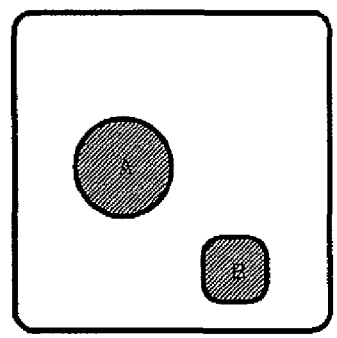

The above first embodiment relates to the case that a single liquid article is inspected at a time. A process of inspecting a plurality of liquid articles at a time will be described with respect to FIGS. 15-18. The second embodiment differs from the first embodiment in that the positions of imaging result displayed on the displayer should correspond to the positions of the articles on the carrier mechanism so that the human operator can ascertain which article is dangerous after the CT image has been obtained. FIG. 15A and FIG. 15B show diagrams of CT images reconstructed in the case that a plurality of liquid articles are to be inspected according to the second embodiment.

For example, if the operator observes the inspected articles on the carrier mechanism from the top, then the positions of respective articles on the CT images of all layers should correspond to the top view of the carrier mechanism.

FIG. 16A to FIG. 16K show the process how to rotate the CT reconstruction images and/or the carrier mechanism to be aligned with the position before CT scanning.

FIG. 16A shows a top view of the carrier mechanism 40 when the first CT imaging starts, in which the angle of the carrier mechanism is denoted by an arrow. FIG. 16B shows the first CT image, in which the rotation range of the carrier mechanism is identified by the dash line. Note that FIG. 16B is aligned to FIG. 16A by conventional CT reconstruction algorithm. FIG. 16C shows the first CT image displayed after the inspection, which is the same as FIG. 17B because no further rotation is needed.

FIG. 16D shows a top view of the carrier mechanism at the $n^{th}$ CT imaging starts. From FIG. 16D it can be seen that the carrier mechanism rotates an angle with respect to that before the first CT imaging. FIG. 16E shows the CT image of FIG. 16D and FIG. 16F shows the $n^{th}$ image displayed on the screen after inspection, which is aligned with the first CT image by rotation.

FIG. 16G shows a top view of the carrier mechanism at the last CT imaging starts. From FIG. 16G it can be seen that the carrier mechanism rotates an angle with respect to that at the first CT imaging starts. FIG. 16H shows the CT image of FIG. 16G, and FIG. 16I shows the last CT image displayed on the screen after inspection, which is aligned with the first layer of the CT image by rotation.

FIG. 16J shows a top view of the carrier mechanism after the last CT imaging ends, in which the carrier mechanism rotates an angle with respect to that before the first CT imaging starts. FIG. 16K shows a top view of the carrier mechanism after inspection, which returns to the position of FIG. 16A.

The basic alignment procedure is: after all the CT imaging, the angles of respective layers of the CT image and the carrier mechanism are adjusted. Firstly, respective layers of the CT images are rotated according to the angles of the carrier mechanism at respective CT imaging starts (the degrees can be obtained by the angle information acquirement unit 54) so that the positions of the same article in the CT image of respective layers are aligned, e.g. with the first layer of CT. Next, the angle of the carrier mechanism is adjusted so that the top view of the carrier mechanism corresponds to the CT image.

For example, assume that N times CT imaging are performed, and the angle of the carrier mechanism is $\alpha_n$ at the $n^{th}$ CT imaging starts, and is $\beta_n$ at the $n^{th}$ CT imaging ends. The carrier mechanism rotates counterclockwise in the top view. In order for the position of the article in the $n^{th}$ CT image to be consistent with that in the first one, the $n^{th}$ CT image rotates by $\alpha_n - \alpha_1$ counterclockwise. And finally the carrier mechanism rotates by $360 - (\beta_N - \alpha_1)$ counterclockwise so as the top view of the carrier mechanism being consistent with the CT image.

Figure 17:
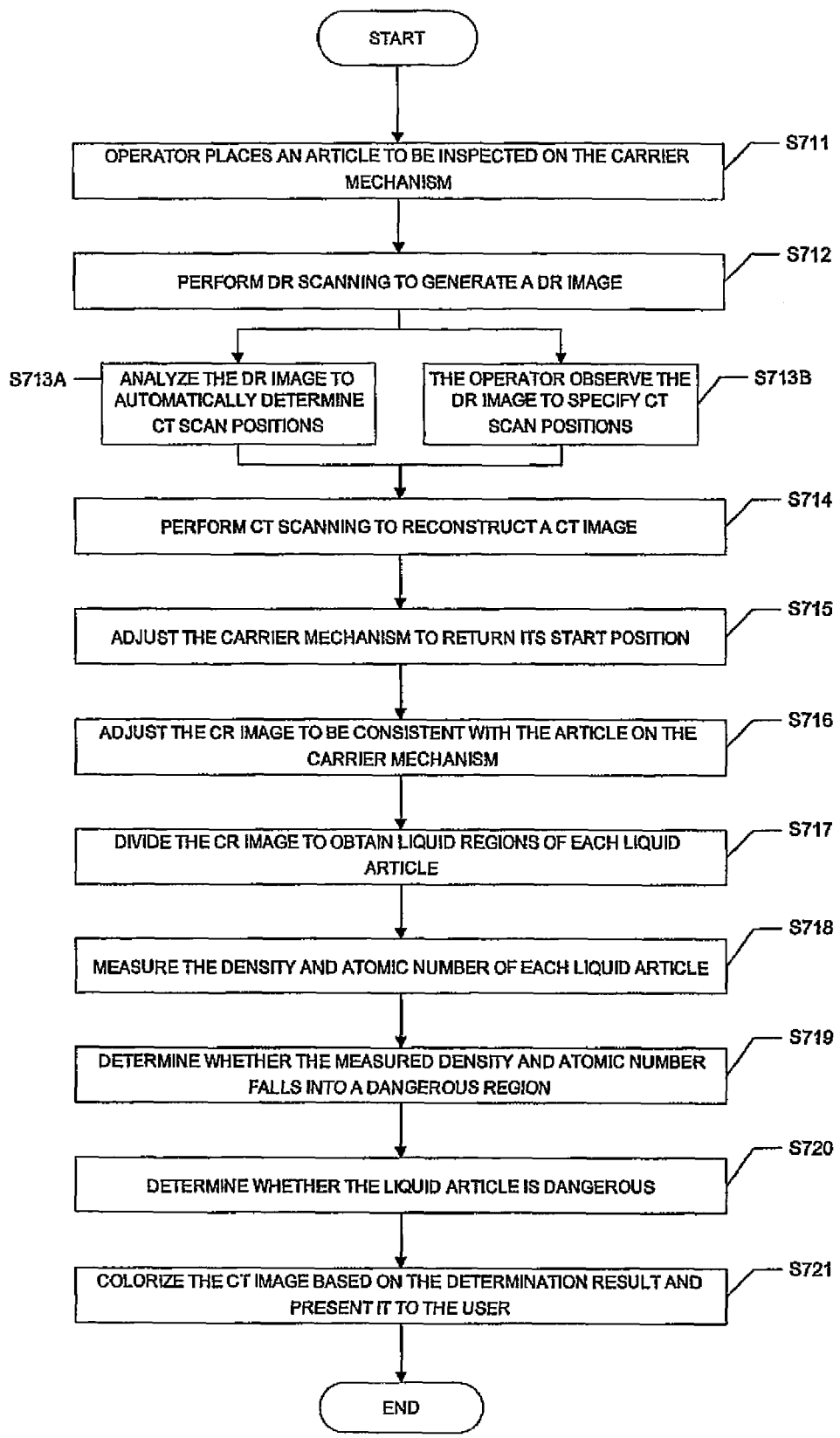
FIG. 17 shows a flowchart for performing inspection operation in the case of there are several articles to be inspected.

FIG. 17 shows a flowchart for performing inspecting operation in the case of a plurality of articles are to be inspected. As shown in FIG. 17, at step S711, the human operator powers on the system and logs in the inspection interface. The system enters into the ready state after self check. Then the operator places the plurality of articles to be inspected, such as article A and article B, on the carrier mechanism 40 and presses an inspection button. Here, assume that the article A is placed at the up right corner of the carrier mechanism, and the article B is placed at the lower left corner of the carrier mechanism.

Next, at step S712, the operator presses a start button to perform DR scanning as described above, to generate a DR image.

After the DR image has been obtained, at step S713A, the DR image is analyzed to automatically determine the scan position of the CT imaging, or at step S713B, the operator operates the input device 65 such as a mouse to specify positions where to perform a CT scanning. In such a way, CT scanning is only performed at typical positions in the liquid articles, whereby the inspection is speeded up without lowering the inspection quality.

Having determining the CT scan positions, a CT scanning process is performed at step S714, i.e. CT scanning is performed at the determined positions in the liquid articles to obtain CT projection data and a CT image is reconstructed based on the CT projection data. Each pixel of the CT image denotes the density and atomic number of corresponding portion in the liquid articles. In the case that the liquid is layered, the CT scanning is repeated for each layer.

After the last CT imaging ends, at step S715 and S716, the carrier mechanism and each layer of the CT image are adjusted as above so that the positions of respective articles in each layer of the CT image are consistent (e.g. aligned with those in the CT image of the first layer), and consistent with the real positions of the articles on the carrier mechanism (e.g. in the top view), thereby article B and article A can be distinguished from each other.

At step S717, image partition processing is preformed on the CT images of each layer (for example, by using a watershed algorithm) to obtain the liquid region of each inspected article. At step 718, the average density and average atomic number of respective pixels in each liquid region are calculated. At step S719, it is determined whether points defined by the measured densities and atomic numbers of respective liquid regions locate at a predetermined region in the density-atomic number coordinate space. At step 720, it is determined whether the liquid of this layer in the inspected article is dangerous based on the result of step S719.

At step S721, the results of respective layers are gathered and shown to the operator. One of the gathering methods is to conclude that the result is "secure" only if all the liquid regions in all the CT images are determined to be secure; otherwise the result is "suspicious". Furthermore, the CT images of respective layers are colorized and displayed to the users. The suspicious articles are shown with a certain color (such as red), and secure liquid are shown with another color (such as green).

Figure 18:
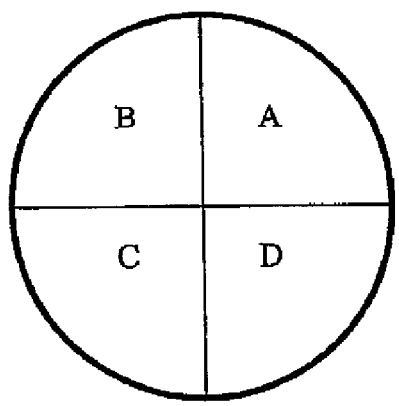
FIG. 18 shows a top view of the carrier mechanism according to a second embodiment of the present invention.

The case in which two liquid articles are inspected is described above. When more liquid articles are to be inspected, a plurality of regions, such as region A, region B, region C and region D shown in FIG. 18, are partitioned in the surface on which the carrier mechanism carries the liquid articles, as shown in FIG. 18, so that the operator can ascertain the positions of respective liquid articles. In this way, the operator can locate respective liquid articles in corresponding regions, and input respective liquid identification information for respective regions.

Third Embodiment

To improve inspection efficiency, and to help slim articles stand stably in the barrel, the third embodiment will employ a divided barrel.

The third embodiment differs from the second one in that a divided barrel is used in the process of inspecting a plurality of articles. The operation of the inspection system according to the third embodiment will be described with respect to FIGS. 19-24.

Figure 19:
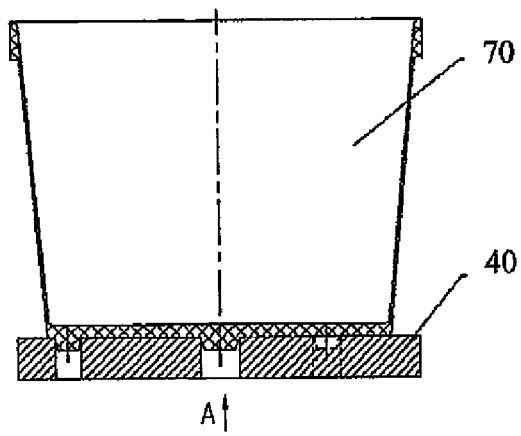
FIG. 19 shows a side view of a divided barrel according to an embodiment of the invention.
Figure 20:
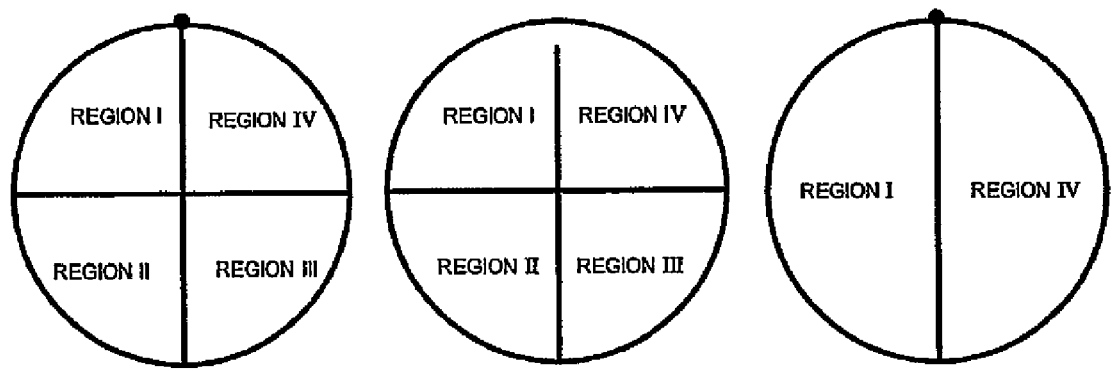
FIG. 20 shows a top view of a divided barrel.
Figure 21:
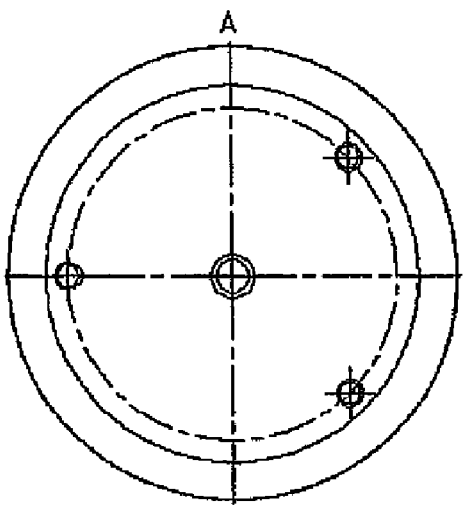
FIG. 21 shows a bottom view of a divided barrel.

FIG. 19 shows a side view of a divided barrel according to an embodiment of the invention, FIG. 20 shows a top view of a divided barrel, and FIG. 21 shows a bottom view of a divided barrel.

As shown in FIG. 19, the divided barrel 70 comprises a bottom and a side wall coupled to the bottom. Protrudes of cone shape or other shape are provided on the lower surface of the bottom. The three cone-shaped protrudes can be inserted into the corresponding location holes on the carrier mechanism 40 so that the divided barrel 70 will rotate as the carrier mechanism 40 during the rotation of the carrier mechanism 40 to prevent relative motion from occurring therebetween.

Moreover, as shown in FIG. 19, a flange is provided along the top of the side wall to facilitate grasp and portage of the operator. The side wall has a sharp of a column or a cone, and is made of materials with elasticity, such as Polyethylene (PE) or aluminum.

FIG. 20 is the top view of three kinds of divided barrels. As shown, one or more dividing parts are provided in the space formed by the bottom and the side wall. The space is divided into plural subspaces to place corresponding liquid articles. In such a way, if a plurality of liquid articles is to be inspected at a time, the liquid articles are placed in the subspaces divided by the dividing parts. In this case, marks can be provided on the outer surface of the side wall to locate the articles in the barrel. For example, when one of four articles is determined to be suspicious, the one can be notified to the operator by the corresponding mark of the article on the side wall.

For example, as shown in left of FIG. 20, mark with round sections of preset sizes are provided at the end of the dividing parts, or one of the dividing parts being shorter than the others is used as the mark for locating liquid articles.

FIG. 21 is a bottom view of a divided barrel. Though three protrudes are provided uniformly at the lower surface of the bottom, the protrudes can also be distributed non-uniformly.

Figure 22:
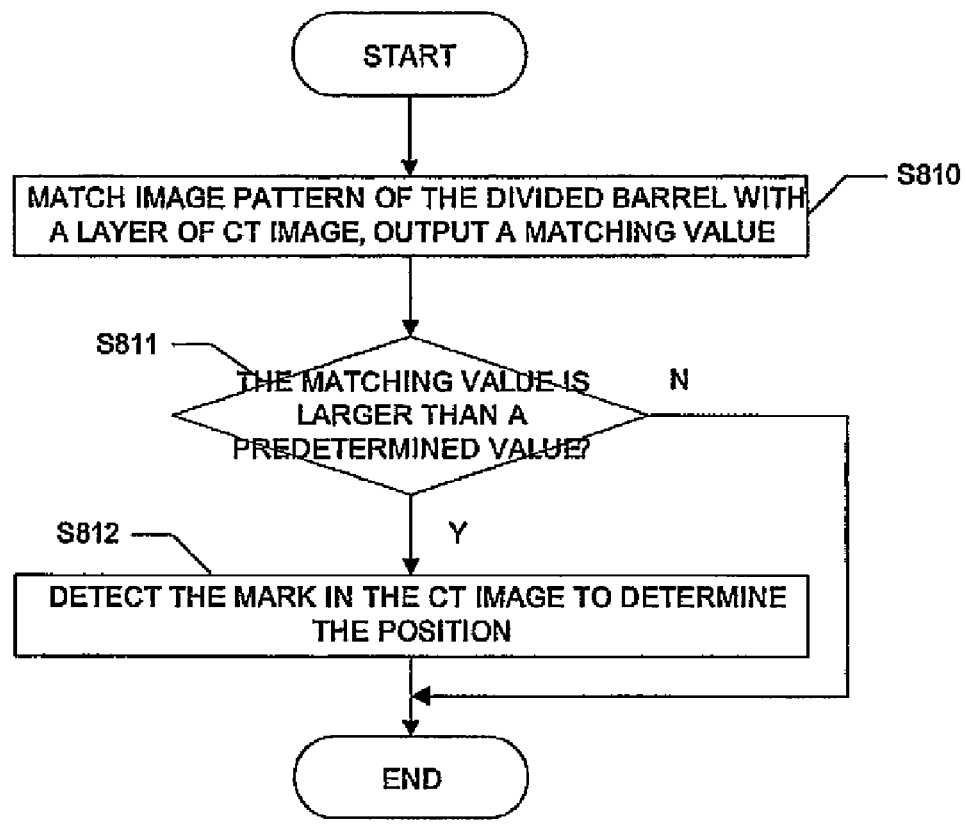
FIG. 22 shows a process how to automatically detect the divided barrel and the mark during an inspection operation.

FIG. 22 shows a process how to automatically detect the divided barrel and the mark during an inspection operation. As described above, the divided barrel can be detected by a pattern matching method which is typical in the image processing because the divided barrel has a specific structure. Taking the first kind of barrel with a cross dividing part as an example, at step S810 a pattern image with a cross can be established at first, and the center of the pattern is placed on the center of the CT image to be identified to obtain a matching value.

At step S811, it is determined whether the matching value is larger than a predetermined threshold or not. If not, then the pattern image is rotated until maximum matching of the pattern image and the CT image is obtained. If the matching is larger than a predetermined threshold, then it is deemed that a divided barrel exists in the CT image; otherwise it is deemed that no divided barrel exists in the CT image.

In the case that a divided barrel exists in the CT image, then at step S812, the location mark can be detected according to the characteristics thereof. Again taking the first kind of barrel with a cross dividing part as an example, the location mark is at top of a dividing line which is longer than other three dividing lines. After it is determined that a divided barrel exists in the CT image through the pattern matching method, the cross line in the pattern image at maximum matching superposes a dividing line. The location mark can be detected by comparing the four dividing lines and taking the longest one.

In the case of a multi-layered CT imaging, firstly divided barrel detection and location mark detection are performed on each layer of the CT image. If no divided barrel is detected in respective layers, then it is deemed that no divided barrel is used by the operator. If a divided barrel is detected in at least one layer, then it is deemed that a divided barrel is used. If detected location mark positions of respective layers are different, then the one with strongest signal intensity can be taken as the final location mark. One method to describe the signal intensity of the location mark in a layer of the CT image is to subtract an average value from the maximum value of the four dividing lines in the layer. The larger the difference is, the stronger the signal intensity of the location mark is.

FIG. 23A to FIG. 23D shows a diagram of a process of rotating the barrel during the inspection operation. The divided barrel is adjusted to a specified position by adjusting the location mark of the barrel to a predetermined position. Taking the first kind of barrel with a cross dividing part as an example, a polar coordinate system is established with the center of the CT image as the origin, positions of each chamber are uniquely determined by the angle coordinates of the location mark. Assume that the angle of the polar coordinate corresponding to the finally determined location mark in the CT image is $\gamma$, and the preset adjustment target of the system is $\theta$, then the adjustment can be done by rotating layers of the CT image and the carrier mechanism by $\theta-\gamma$, as shown in FIG. 24 below.

Figure 23A:
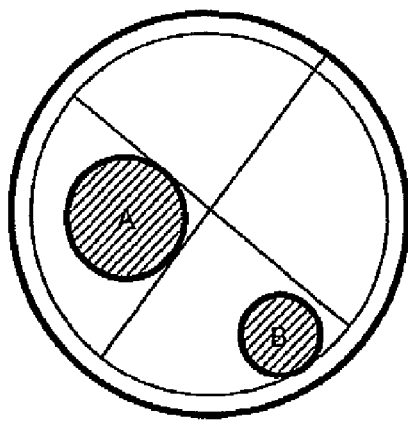
FIG. 23A to FIG. 23D shows a diagram of a process of rotating the barrel during the inspection operation.
Figure 23B:
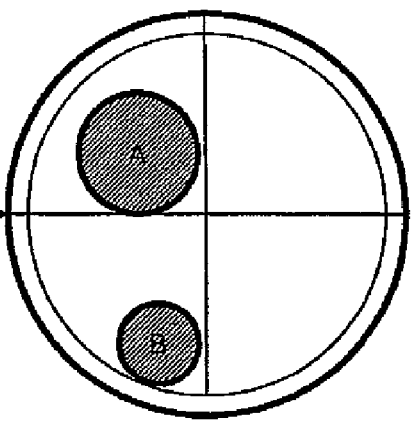
Figure 23C:
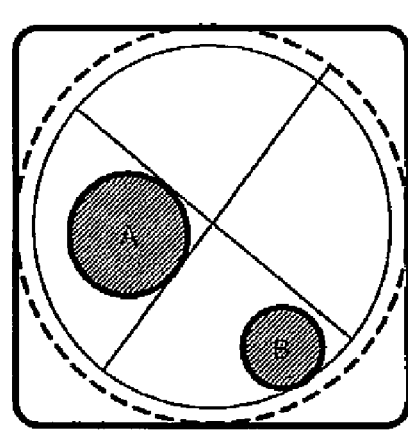
Figure 23D:
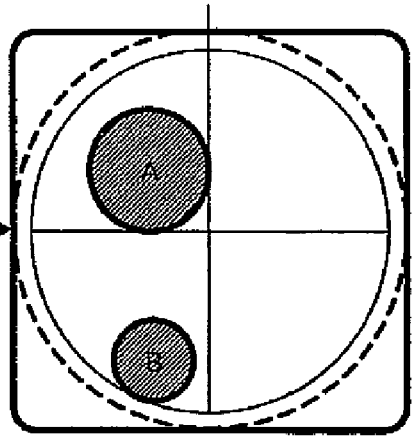

As shown in FIGS. 23A and 23B, the divided barrel rotates a certain angle to reach a preset position. Similarly, each layer of the CT image rotates to be aligned with the rotated divided barrel.

Figure 24:
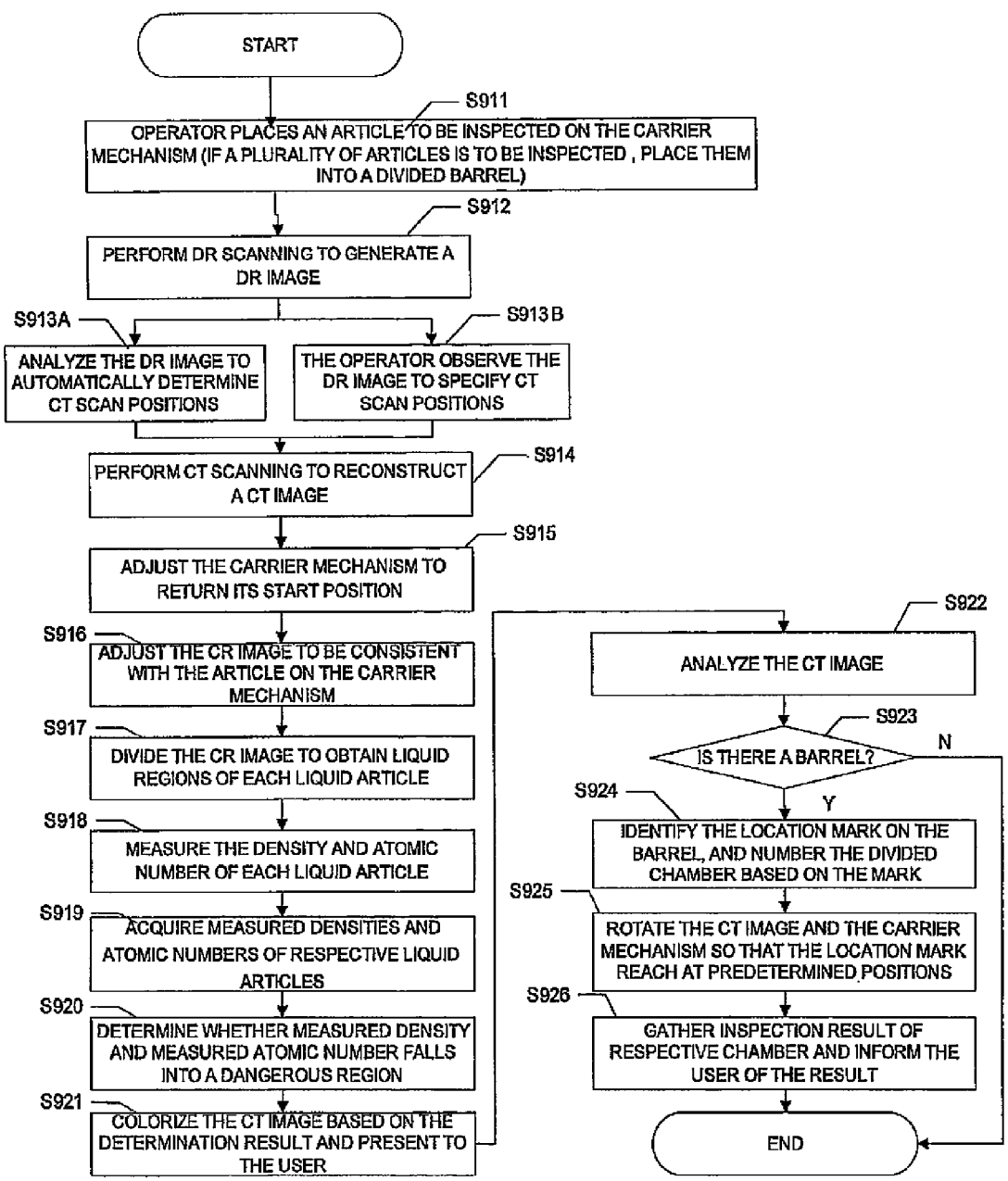
FIG. 24 shows a flowchart of the inspection operation according to a third embodiment of the invention.

FIG. 24 shows a flowchart of the inspection operation according to a third embodiment of the invention. Steps S911 to S921 are the same as steps S711 to S721 in the above second embodiment. Only steps S922 to S926 will be described.

At step S922, the CT image is analyzed. At step S923, it is determined whether there is a divided barrel. In the case of no divided barrel, then the inspection operation ends.

If a barrel is used, then at step S924, the location mark of the barrel is identified to determine the positions of each chamber. Next, at step S925, the carrier mechanism and each layer of the CT image are further adjusted so that each chamber of the barrel on the carrier mechanism and each chamber on each layer of the CT image reach predetermined positions.

At step S926, the system lists the results of respective liquid regions of each layer of the CT image in each chamber, and gathers them to display to the user. One gathering method according to the embodiment is to conclude that the result of a chamber is "secure" only if all the liquid regions of all the CT images in this chamber are determined to be secure; otherwise the result of the chamber is "suspicious".

[First Variation]

Though the present invention is described with respect to the case of first DR imaging and then CT imaging, spiral CT imaging also can be adopted to inspect liquid articles according to the present invention.

Figure 25:
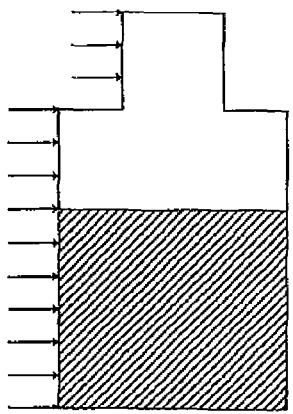
FIG. 25 is a diagram for explaining the spiral CT scanning process of the liquid article.
Figures 26A, 26B, 26C, 26D:
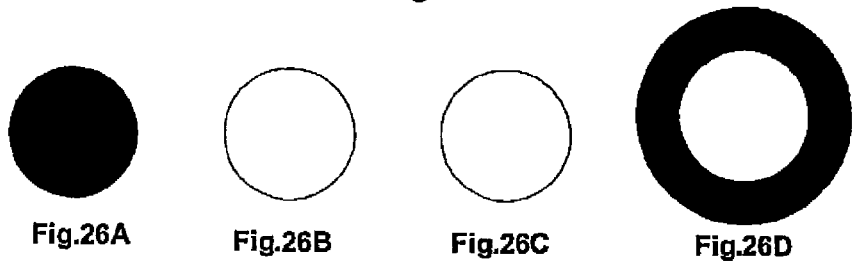
FIG. 26A to FIG. 26M are diagrams illustrating the images obtained by performing spiral CT scanning on the liquid article.
Figures 26E, 26F, 26G:
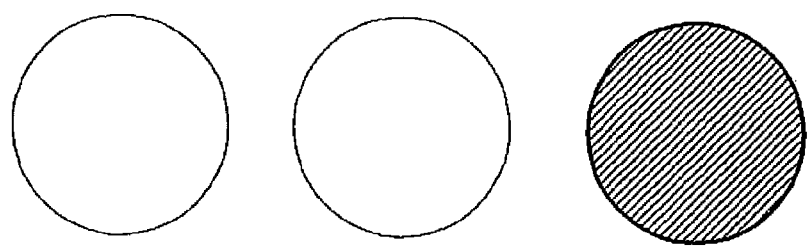
Figures 26H, 26I, 26J:
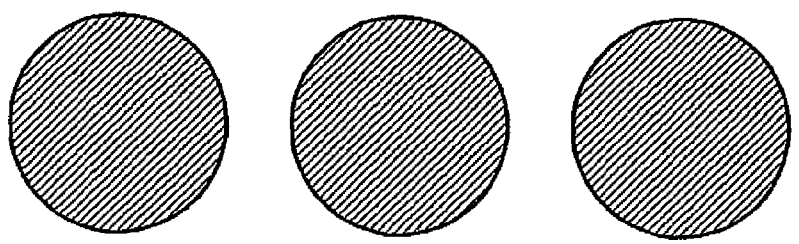
Figures 26K, 26L, 26M:
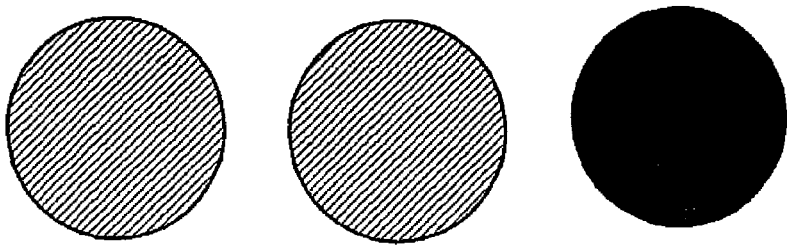

A set of spiral CT images can be obtained by performing CT on liquid article. The position of the liquid in the liquid article can be determined by comparing and analyzing pixels in the set of CT images, and whether the liquid is layered can also be determined. The physical attributes, such as density and atomic number, of the liquid of respective positions can be obtained in a similar manner as described above. For example, when spiral CT imaging is performed on the liquid article shown in FIG. 25, and the spiral pitch is 2 cm, then a set of CT images as shown in FIGS. 26A-26M can be obtained. In this way, the position of the liquid in the liquid article can be obtained by analyzing pixels in the spiral CT images. Here, the spiral CT imaging can be high pitch CT imaging or normal pitch CT imaging.

As known to those skilled in the art, the above variant embodiment is applicable in the case of multiple article inspection as the second embodiment and the third embodiment are.

Moreover, though the above description takes the density and atomic number as examples, the present invention is also effective when only one attribute, either the density or atomic number, is used, or even more physical attributes are used to identify dangerous articles. In the former case, whether the liquid is dangerous is determined by determining whether the one physical attribute locates at a predetermined region. In the latter case, whether the liquid is dangerous is determined by determining a point defined by the physical attributes locates at a predetermined region in a multi dimensional space defined by these attributes.

[Second Variation]

Though in the above description first the DR imaging and then dual-energy CT imaging are performed to acquire the density and atomic number of the liquid, the DR imaging is optional. Predetermined positions where to perform dual-energy CT imaging can be specified in advance for various liquid articles to acquire the density and atomic number of the liquid.

While exemplary embodiments of the present invention have been described hereinabove, it should be clear to those skilled in the art that any variations and/or modifications of the basic inventive concepts will still fall within the scope of the present invention, as defined in the appended claims.

What is claimed is:

1. A method of inspecting a liquid article comprising:
    performing a DR imaging on the liquid article to generate a transmission image;
    determining from the transmission image at least one positions at which CT scan is to be performed;
    performing dual-energy CT scan at the determined positions to generate CT image data;
    determining a density and atomic number from the generated CT image data;
    judging whether at least one point defined by the density and the atomic number determined from the CT image data falls into a predetermined region in a two-dimensional space of density-atomic number; and
    outputting information indicative of that the liquid article is dangerous or not.

2. The method of claim 1, wherein the step of determining comprises:
    analyzing the transmission image using an image processing technique to obtain information about at least one liquid portion in the liquid article as analysis results; and
    determining the positions based on the analysis results.

3. The method of claim 2, wherein the information about the liquid portion comprises location information of the at least one liquid portions in the liquid article, and at least one positions is determined based on the location information of the at least one liquid portions in the liquid article.

4. The method of claim 1, wherein the step of determining comprises:
    displaying the transmission image; and
    receiving the at least one positions set with respect to the transmission image using an input device.

5. The method of claim 4, wherein, in the case of the transmission image shows that the liquid are layered, at least one line in each layer of the liquid portions is set as the positions.

6. The method of claim 1, wherein the step of performing dual-energy CT scan comprises:
    performing a dual-energy CT scan on the liquid article to generate a high-energy CT image data and a low-energy CT image data; and taking one of the high-energy CT image data, low-energy CT image data and the combination of the high-energy CT image data and the low-energy CT image data as the CT image data.

7. An apparatus of inspecting a liquid article comprising:
a radiation source adapted to emit radiation beams;
a detection and acquisition device adapted to detect and acquire radiation signals transmitted through the liquid article;
a controller adapted to control the detection and acquisition device to perform DR imaging on the liquid article to generate a transmission image, and perform CT imaging on the liquid article at least one positions to generate CT image data;
a computer adapted to determine a density and atomic number from the generated CT image data, judge whether at least one point defined by the density and the atomic number determined from the CT image data falls into a predetermined region in a two-dimensional space of density, and output information indicative of that the liquid article is dangerous or not,
wherein the computer is further adapted to send to the controller a signal to indicate at least one positions at which the CT scan is performed.

8. The apparatus of claim 7, wherein the computer is further adapted to analyze the transmission image using an image processing technique to obtain information about at least one liquid portions in the liquid article as analysis results, and determine the positions based on the analysis results.

9. The apparatus of claim 8, wherein the information about the liquid portion comprises location information of at least one liquid portions in the liquid article, and the computer is further adapted to determine the at least'one positions based on the location information of the liquid portions in the liquid article.

10. The apparatus of claim 7, wherein the computer comprises:
a display device that displays the transmission image;
an input device that receives the positions set with respect to the transmission image at which the CT scan is to be performed.

11. The apparatus of claim 10, wherein in the case of the transmission image shows that the liquid are layered, at least one line in each layer of the liquid portions is set as the positions.

12. The apparatus of claim 7, wherein the controller is further adapted to control the radiation source and the detection and acquisition device to perform a dual-energy CT scan on the liquid article to generate a high-energy CT image data and a low-energy CT image data; and
the computer is further adapted to take one of the high-energy CT image data, low-energy CT image data and the combination of the high-energy CT image data and the low-energy CT image data as the CT image data.

13. A method of inspecting a plurality of liquid articles, comprising:
placing a barrel which is divided into a plurality of sub-spaces on a carrying stage, wherein the plurality of liquid articles are disposed in the respective sub-spaces, and at least one specific mark is provided for the barrel;
performing a CT scan on the liquid articles at at least one positions to generate CT image data;
determining whether one or more liquid article is dangerous or not based on the CT image data;
analyzing the CT image data to determine the location of the specific mark in the CT image; and
determining locations of the one or more liquid articles in the barrel in accordance with the locations of the liquid articles relative to the specific mark in the CT image.

14. The method of claim 13, wherein the specific mark is set at the wall of the barrel.

15. The method of claim 13, wherein the step of performing a CT scan comprises:
performing a dual-energy CT scan on the liquid article to generate a high-energy CT image data and a low-energy CT image data; and
taking one of the high-energy CT image data, low-energy CT image data and the combination of the high-energy CT image data and the low-energy CT image data as the CT image data.

16. The method of claim 13, wherein the step of analyzing comprises:
determining the locations of the specific mark in the CT image using template matching method.

17. A method of inspecting a plurality of liquid articles, comprising:
placing a plurality of liquid articles in the respective regions of a carrying stage, wherein the regions are colored to distinguish from each other;
performing CT scan on the liquid articles at at least one positions to determine whether at least one of the plurality of the liquid articles is dangerous or not; and
associating the dangerous liquid article with the respective region on the carrying stage.

18. The method of claim 17, wherein in the case of performing a plurality of CT scans at different positions, the CT image is rotated after every CT scan such that the CT image is aligned with the image generated from the first CT scan.

19. The method of claim 18, wherein the after dual-energy CT scan at the positions, the inspected liquid article is rotated to the position before scan.

20. A method of inspecting a plurality of liquid articles, comprising:
placing a plurality of liquid articles on a carrying stage;
performing CT scan on the liquid articles at a plurality of positions of the liquid articles to generate CT images;
after each CT scan, rotating the CT image of the liquid articles to be aligned with each other and to be aligned with the final position of the liquid articles on the carrying stage;
analyzing CT images to determine whether at least one liquid article is dangerous or not; and
displaying the CT image of the dangerous liquid article in a visually distinguishable manner.

21. The method of claim 20, wherein the step of performing CT scan comprises:
performing a dual-energy CT scan on the liquid article at a plurality of positions to generate a high-energy CT image data and a low-energy CT image data; and
taking one of the high-energy CT image data, low-energy CT image data and the combination of the high-energy CT image data and the low-energy CT image data as the CT image data.

22. The method of claim 20, wherein the plurality of liquid articles is disposed in a plurality of regions which are colored to distinguish from each other, the method further comprises:
associating the image of the dangerous liquid article with the region in which the liquid article is disposed.

23. The method of claim 20, wherein the step of analyzing comprises:

analyzing the CT image data to obtain the physical attribute values about the liquid article, wherein the physical attribute values comprises atomic number and density; and determining whether the at least one liquid article is dangerous by judging whether at least one point defined by the density and the atomic number derived from the CT image data falls into a predetermined region in a density-atomic number two-dimensional space.

24. A method of inspecting a liquid article, comprising:

retrieving position information of a liquid portion in accordance with information acquired from outside of the liquid article;

placing the liquid article on a carrying stage;

determining positions at which CT scan are to be performed based on the position information;

performing CT scan on the liquid article at the positions to obtain CT image data; and analyzing the CT image data to determine whether the liquid article is dangerous or not.

25. The method of claim 24, wherein the information acquired from outside of the liquid article comprises at least one of types of product, producer and size.

26. The method of claim 24, wherein the step of performing CT scan comprising:

performing a dual-energy CT scan on the liquid article to generate a high-energy CT image data and a low-energy CT image data; and taking one of the high-energy CT image data, low-energy CT image data and the combination of the high-energy CT image data and the low-energy CT image data as the CT image data.

27. The method of claim 24, wherein the step of analyzing comprises:

analyzing the CT image data to obtain the physical attribute values about the liquid article, wherein the physical attribute values comprises at least one of atomic number and density; and determining whether the at least one liquid article is dangerous or not by judging whether at least one point defined by the density and the atomic number derived from the CT image data falls into a predetermined region in a density-atomic number two-dimensional space.

* * * * *